(12) United States Patent
Matsui et al.

(10) Patent No.: US 11,579,529 B2
(45) Date of Patent: Feb. 14, 2023

(54) POSITIVE RESIST COMPOSITION AND PATTERNING PROCESS

(71) Applicant: Shin-Etsu Chemical Co., Ltd., Tokyo (JP)

(72) Inventors: Yoshinori Matsui, Joetsu (JP); Masayoshi Sagehashi, Joetsu (JP); Tatsushi Kaneko, Joetsu (JP); Akihiro Seki, Joetsu (JP); Satoshi Watanabe, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 416 days.

(21) Appl. No.: 16/800,478

(22) Filed: Feb. 25, 2020

(65) Prior Publication Data

US 2020/0285152 A1 Sep. 10, 2020

(30) Foreign Application Priority Data

Mar. 6, 2019 (JP) .............................. JP2019-040330

(51) Int. Cl.

| | |
|---|---|
| *G03F 7/039* | (2006.01) |
| *G03F 7/004* | (2006.01) |
| *C07D 303/40* | (2006.01) |
| *C08F 220/18* | (2006.01) |
| *C08F 220/28* | (2006.01) |
| *G03F 7/16* | (2006.01) |
| *G03F 7/32* | (2006.01) |

(Continued)

(52) U.S. Cl.
CPC ......... *G03F 7/0397* (2013.01); *C07D 303/40* (2013.01); *C08F 220/1805* (2020.02); *C08F 220/283* (2020.02); *G03F 7/0045* (2013.01); *G03F 7/162* (2013.01); *G03F 7/168* (2013.01); *G03F 7/201* (2013.01); *G03F 7/2004* (2013.01); *G03F 7/2006* (2013.01); *G03F 7/2037* (2013.01); *G03F 7/322* (2013.01); *G03F 7/38* (2013.01)

(58) Field of Classification Search
CPC ........ G03F 7/11; G03F 7/0395; G03F 7/0397; C07C 381/12
See application file for complete search history.

(56) References Cited

U.S. PATENT DOCUMENTS

| | | | |
|---|---|---|---|
| 6,265,131 B1 | 7/2001 | Chang et al. | |
| 6,492,091 B2 | 12/2002 | Kodama et al. | |
| | (Continued) | | |

FOREIGN PATENT DOCUMENTS

| | | |
|---|---|---|
| JP | 3790649 B2 | 6/2006 |
| JP | 2007-145797 A | 6/2007 |
| | (Continued) | |

OTHER PUBLICATIONS

Lin, "Semiconductor Foundry, Lithography, and Partners", Proc. SPIE, 2002, vol. 4690, xxix, cited in Specification (14 pages).

(Continued)

*Primary Examiner* — Amanda C. Walke
(74) *Attorney, Agent, or Firm* — WHDA, LLP

(57) ABSTRACT

A positive resist composition is provided comprising two onium salts, a base polymer comprising acid labile group-containing recurring units, and an organic solvent. The positive resist composition forms a pattern having PED stability and improved properties including DOF, LWR, and controlled footing profile.

9 Claims, 1 Drawing Sheet

(51) Int. Cl.
*G03F 7/20* (2006.01)
*G03F 7/38* (2006.01)

(56) References Cited

U.S. PATENT DOCUMENTS

| | | | |
|---|---|---|---|
| 7,511,169 B2 | 3/2009 | Ohsawa et al. | |
| 8,173,354 B2 | 5/2012 | Ohsawa et al. | |
| 8,394,570 B2 | 3/2013 | Ohashi et al. | |
| 8,535,869 B2 | 9/2013 | Ohsawa et al. | |
| 8,900,796 B2 | 12/2014 | Ohashi et al. | |
| 9,086,628 B2* | 7/2015 | Suka | G03F 7/11 |
| 9,507,259 B2* | 11/2016 | Li | G03F 7/004 |
| 9,904,167 B2* | 2/2018 | Tsuchimura | C07J 41/0061 |
| 2005/0181299 A1 | 8/2005 | Trefonas et al. | |
| 2011/0171576 A1* | 7/2011 | Yamaguchi | G03F 7/0045 544/158 |
| 2011/0201823 A1* | 8/2011 | Yoshida | G03F 7/0045 548/334.1 |
| 2012/0122032 A1* | 5/2012 | Anryu | C07D 327/06 549/13 |
| 2012/0258403 A1* | 10/2012 | Anryu | C07C 303/32 544/58.7 |
| 2014/0199630 A1* | 7/2014 | Ohashi | C07C 309/06 549/80 |
| 2015/0301449 A1* | 10/2015 | Ohashi | G03F 7/0045 430/296 |
| 2016/0200702 A1* | 7/2016 | Sakamoto | G03F 7/0046 549/14 |
| 2017/0131634 A1 | 5/2017 | Nakagawa et al. | |
| 2017/0351177 A1* | 12/2017 | Hatakeyama | G03F 7/0048 |
| 2019/0377261 A1 | 12/2019 | Sakita et al. | |
| 2020/0159115 A1* | 5/2020 | Ono | C07C 309/12 |
| 2020/0283400 A1* | 9/2020 | Sagehashi | G03F 7/0045 |
| 2020/0285152 A1 | 9/2020 | Matsui et al. | |

FOREIGN PATENT DOCUMENTS

| | | | | |
|---|---|---|---|---|
| JP | 4226803 B2 | | 2/2009 | |
| JP | 2011-16746 A | | 1/2011 | |
| JP | 2012046501 A | * | 3/2012 | C07C 309/14 |
| JP | 5246220 B2 | | 7/2013 | |
| JP | 2013-209360 A | | 10/2013 | |
| JP | 5471363 B2 | | 4/2014 | |
| JP | 2020-149048 A | | 9/2020 | |
| KR | 2011083525 A | * | 7/2011 | C07D 295/088 |
| TW | 202024030 A | * | 7/2020 | C07C 309/12 |
| WO | 2018/180070 A1 | | 10/2018 | |

OTHER PUBLICATIONS

Non-Final Office Action dated Mar. 18, 2022, issued in U.S. Appl. No. 16/800,447. (18 pages).
Office Action dated Dec. 14, 2021, issued in JP application No. 2019-040260 (counterpart to U.S. Appl. No. 16/800,447, with English translation. (5 pages).

* cited by examiner

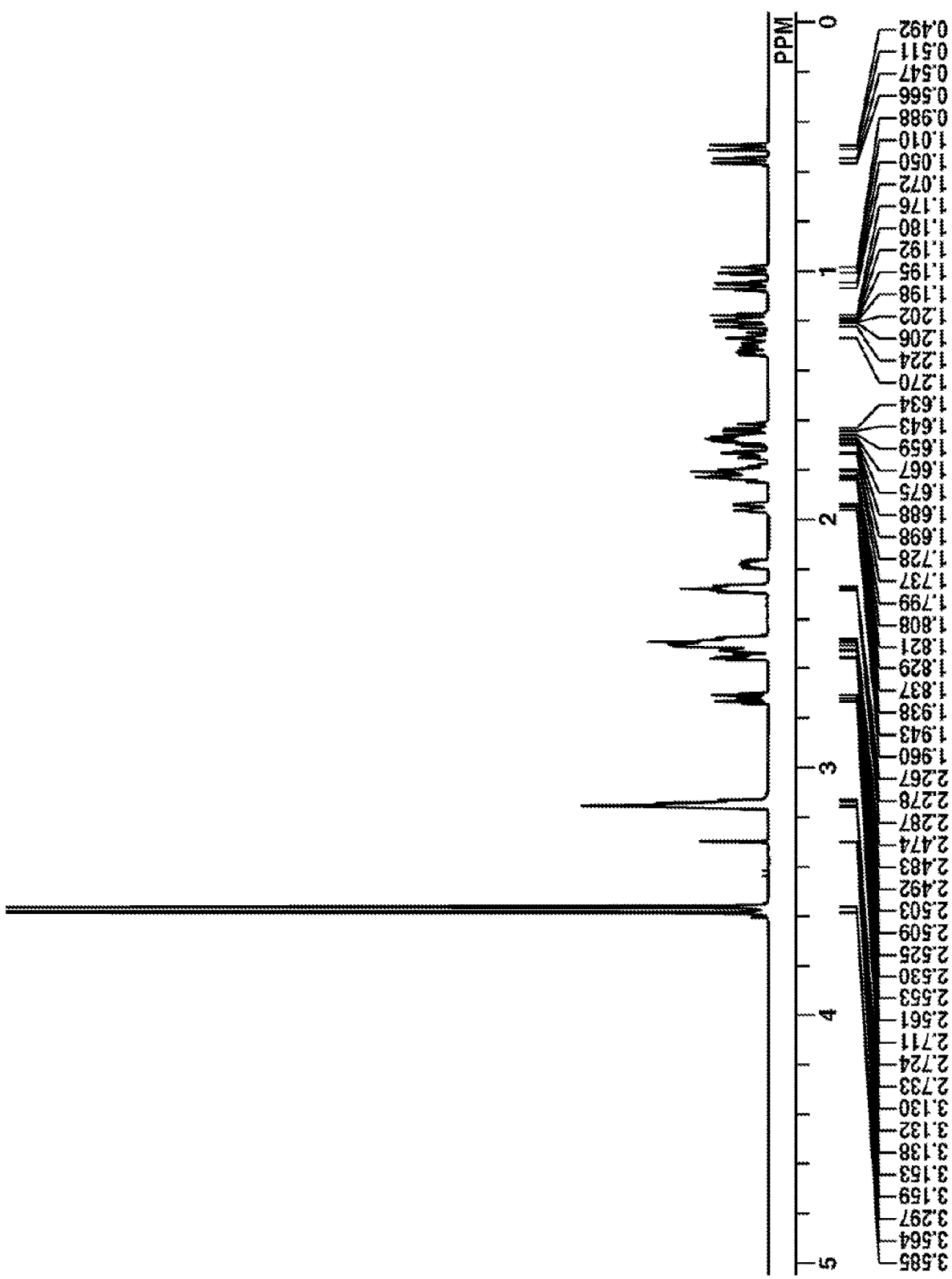

POSITIVE RESIST COMPOSITION AND PATTERNING PROCESS

CROSS-REFERENCE TO RELATED APPLICATION

This non-provisional application claims priority under 35 U.S.C. § 119(a) on Patent Application No. 2019-040330 filed in Japan on Mar. 6, 2019, the entire contents of which are hereby incorporated by reference.

TECHNICAL FIELD

This invention relates to a positive resist composition and a pattern forming process.

BACKGROUND ART

In the recent drive for higher integration and operating speeds of LSI and memory devices, the pattern rule is made drastically finer. The photolithography which is currently on widespread use in the art is approaching the essential limit of resolution determined by the wavelength of a light source.

As the light source used in the lithography for resist pattern formation, g-line (436 nm) or i-line (365 nm) from a mercury lamp was widely used in 1980's. Reducing the wavelength of exposure light was believed effective as the means for further reducing the feature size. For the mass production process of 64 MB dynamic random access memories (DRAM, processing feature size 0.25 µm or less) in 1990's and later ones, the exposure light source of i-line (365 nm) was replaced by a KrF excimer laser having a shorter wavelength of 248 nm.

However, for the fabrication of DRAM with a degree of integration of 256 MB and 1 GB or more requiring a finer patterning technology (processing feature size 0.2 µm or less), a shorter wavelength light source was required. Over the decades, photolithography using ArF excimer laser light (193 nm) has been under active investigation. It was expected at the initial that the ArF lithography would be applied to the fabrication of 180-nm node devices. However, the KrF excimer lithography survived to the mass-scale fabrication of 130-nm node devices. So, the full application of ArF lithography started from the 90-nm node. The ArF lithography combined with a lens having an increased numerical aperture (NA) of 0.9 is considered to comply with 65-nm node devices. For the next 45-nm node devices which required a father reduction of exposure light wavelength, the $F_2$ lithography of 157 nm wavelength became a candidate. However, for the reasons that the projection lens uses a large amount of expensive $CaF_2$ single crystal, the scanner thus becomes expensive, hard pellicles are introduced due to the extremely low durability of soft pellicles, the optical system must be accordingly altered, and the etch resistance of resist is low; the development of $F_2$ lithography was stopped and instead, the ArF immersion lithography was introduced. See Non-Patent Document 1.

In the ArF immersion lithography which has been commercially implemented over the decade, exposure is performed while the space between the projection lens and the wafer is filled with water having a refractive index of 1.44. As compared with the conventional ArF lithography wherein the space between the projection lens and the wafer is filled with air having a refractive index of 1, the ArF immersion lithography enables high resolution exposure because the incident angle of exposure light onto the wafer is mitigated to provide a high NA of at least 1.

One candidate for the 32-nm node lithography is lithography using extreme ultraviolet (EUV) radiation with wavelength 13.5 nm. The EUV lithography has many accumulative problems to be overcome, including high power laser, high sensitivity, high resolution and minimized edge roughness (LER, LWR) of resist film, defect-free MoSi laminate mask, low aberration reflection mirror, pellicle, and the like.

Another candidate for the 32-nm node lithography is high refractive index immersion lithography. The development of this technology was stopped because lutetium aluminum garnet (LuAG), a high refractive index lens candidate had a low transmittance and the refractive index of liquid did not reach the goal of 1.8.

The process that now draws attention under the above-discussed circumstances is a double patterning process involving a first set of exposure and development to form a first pattern and a second set of exposure and development to form pattern features just between the first pattern features. A number of double patterning processes are proposed. One exemplary process involves a first set of exposure and development to form a photoresist pattern having lines and spaces at intervals of 1:3, processing the underlying layer of hard mask by dry etching, applying another layer of hard mask thereon, a second set of exposure and development of a photoresist film to form a line pattern in the spaces of the first exposure, and processing the hard mask by dry etching, thereby forming a line-and-space pattern at a half pitch of the first pattern. An alternative process involves a first set of exposure and development to form a photoresist pattern having spaces and lines at intervals of 1:3, processing the underlying layer of hard mask by dry etching, applying a photoresist layer thereon, a second set of exposure and development to form a second space pattern on the remaining hard mask portion, and processing the hard mask by dry etching. In either process, the hard mask is processed by two dry etchings.

In the litho-litho-etch (LLE) double patterning technology including patterning by first exposure and subsequent patterning by second exposure, the development of the first photoresist pattern is eliminated or postponed, and development is first performed after the second pattern formation. While the double patterning technology suffers from the problem of increased manufacturing cost due to the complication of the process, the LLE double patterning technology is attractive in that pattern formation is possible through a few steps.

The problem of LLE arises from a lapse of time between first exposure and post-exposure bake (PEB) because second exposure must be interposed therebetween. During the time lapse, the generated acid causes excessive progress of reaction within the resist film or reacts with airborne impurities (e.g., amine compounds) so that it is deactivated. This prohibits resist pattern formation or invites sensitivity changes. To overcome such problems, the resist composition must have post-exposure delay stability (PED stability). It is noted that the PED stability refers to stability to the phenomenon that during the time delay between exposure and PEB, the excessive progress of reaction within the resist film caused by the generated acid or the deactivation of the generated acid by reaction with airborne impurities can prohibit resist pattern formation or invite sensitivity changes.

Under the circumstance where miniaturization of the pattern rule is required in the recent demand for higher integration and operating speeds of LSI and memory devices, it is important to reduce not only the cell area, but also the area of a peripheral circuit. To this end, miniaturization of a two-dimensional pattern that constitutes the peripheral region is required. In turn, the resist composition is required to meet such properties as DOF, LWR, and controlled footing of pattern profile.

For the purpose of solving the above problems, studies are made on photoacid generators. PAGs commonly used in ArF lithography chemically amplified resist compositions are triphenylsulfonium salts which remain stable in resist compositions, as disclosed in Patent Document 1. Since the triphenylsulfonium salts, however, are absorptive at the wavelength (193 nm) of the ArF lithography, there are drawbacks such as reduced transmittance of resist film and low resolution. To achieve a high sensitivity and resolution, 4-alkoxynaphthyl-1-tetrahydrothiophenium cations were developed. To comply with the recent advance of miniaturization. Patent Document 2 discloses a resist composition for the ArF immersion lithography comprising an onium salt of 4-alkoxynaphthyl-1-tetrahydrothiophenium cation and a resin having an acid labile group. Yet there is not available a resist composition capable of meeting such properties as DOF, LWR, and controlled footing of pattern profile as well as PED stability.

For the purpose of solving the above problems, studies are also made on quenchers. As the quencher, not only amine compounds, but also weak acid onium salts are reported. For example, Patent Document 3 describes a positive photosensitive composition for the ArF excimer laser lithography comprising an onium salt of carboxylic acid. This is based on the mechanism that a salt exchange takes place between the weak acid onium salt and a strong acid (sulfonic acid) which is generated from another PAG upon exposure, so that the strong acid having high acidity (α,α-difluorosulfonic acid) is converted to weak acid (alkanesulfonic acid or carboxylic acid), for thereby suppressing acid-aided decomposition reaction of acid labile groups and reducing or controlling the acid diffusion distance. For enhancing the acid diffusion controlling effect, Patent Document 4 discloses a weak acid onium salt having a nitrogen-containing anion.

With the latest further advance of miniaturization, even a resist composition comprising a weak acid onium salt still fails to meet such properties for the ArF immersion lithography as DOF, LWR, and controlled footing of pattern profile as well as PED stability.

Patent Document 5 discloses a resist composition comprising two acid generators having different acidity. This resist composition still fails to meet DOF, controlled footing and PED stability.

CITATION LIST

Patent Document 1: JP-A 2007-145797 (U.S. Pat. No. 7,511,169)
Patent Document 2: JP 5246220
Patent Document 3: JP 4226803 (U.S. Pat. No. 6,492,091)
Patent Document 4: JP-A 2013-209360
Patent Document 5: WO 2018/180070
Non-Patent Document 1: Proc. SPIE Vol. 4690 xxix, 2002

DISCLOSURE OF INVENTION

An object of the invention is to provide a positive resist composition having PED stability, improved DOF and LWR properties, and capable of forming a pattern of controlled footing profile, and a pattern forming process using the resist composition.

The inventors have found that a positive resist composition comprising two onium salts, and a base polymer comprising recurring units having a carboxyl group (or soluble group) protected with a specific acid labile group is quite effective for precise micropatterning because of improved LWR, DOF and PED stability.

In one aspect, the invention provides a positive resist composition comprising:

(A) 4.1 to 20 parts by weight of a first onium salt having the formula (1),
(B) 2.3 to 8.8 parts by weight of a second onium salt having the formula (2),
(C) 80 parts by weight of a base polymer adapted to increase alkaline solubility under the action of acid, the base polymer comprising acid labile group-containing recurring units having the formula (a) and optionally acid labile group-containing recurring units having the formula (b), with the proviso that when the acid labile group-containing recurring units having formula (b) are included, those recurring units containing an acid labile group of at least 14 carbon atoms may be included in an amount of up to 5 mol % of the overall recurring units, and
(D) 200 to 5,000 parts by weight of an organic solvent.

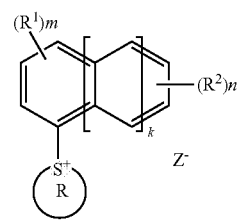

(1)

Herein $R^1$ and $R^2$ each are a hydroxyl group or a $C_1$-$C_{30}$ monovalent hydrocarbon group which may contain a heteroatom, R forms an aliphatic ring of 4 or 5 carbon atoms with $S^+$, m and n each are 0 or 1, k is 0 or 1, and $Z^-$ is an organic anion.

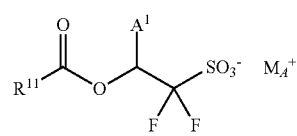

(2)

Herein $A^1$ is hydrogen or trifluoromethyl, $R^{11}$ is a nitrogen-containing heterocyclic group or a group having the formula (2-1):

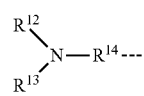

(2-1)

wherein $R^{12}$ and $R^{13}$ are each independently hydrogen or a $C_1$-$C_{20}$ monovalent hydrocarbon group which may contain a heteroatom, $R^{12}$ and $R^{13}$ may bond together to form a ring with the nitrogen atom to which they are attached, $R^{14}$ is a $C_1$-$C_{20}$ divalent hydrocarbon group which may contain a heteroatom, the broken line designates a valence bond, and $M_A^+$ is a sulfonium cation having the formula (2A) or iodonium cation having the formula (2B):

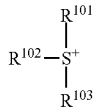
(2A)

(2B)

wherein $R^{101}$, $R^{102}$, $R^{103}$, $R^{104}$ and $R^{105}$ are each independently a $C_1$-$C_{20}$ monovalent hydrocarbon group which may contain a heteroatom, any two or more of $R^{101}$, $R^{102}$ and $R^{103}$ may bond together to form a ring with the sulfur atom to which they are attached.

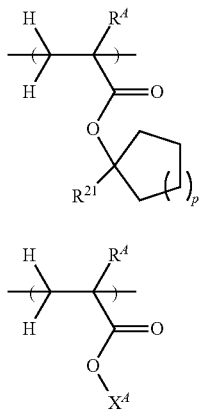

(a)

(b)

Herein $R^A$ is hydrogen or methyl, $R^{21}$ is a $C_1$-$C_8$ straight or branched alkyl group, p is an integer of 1 to 3, and $X^A$ is an acid labile group other than the group having the formula (b1):

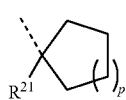
(b1)

wherein $R^{21}$ and p are as defined above, and the broken line designates a valence bond.

In a preferred embodiment, $X^A$ is an acid labile group having the formula (L1), (L2) or (L3).

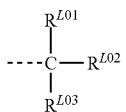
(L1)

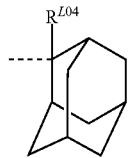
(L2)

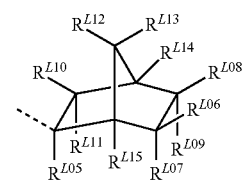
(L3)

Herein the broken line designates a valence bond, $R^{L01}$ to $R^{L03}$ are each independently hydrogen or a $C_1$-$C_{12}$ alkyl group, $R^{L04}$ is hydrogen or a $C_1$-$C_3$ straight or branched alkyl group, $R^{L05}$ to $R^{L15}$ are each independently hydrogen or a $C_1$-$C_6$ monovalent hydrocarbon group.

In a preferred embodiment, the base polymer further comprises recurring units of at least one type selected from recurring units having the formulae (c) to (e).

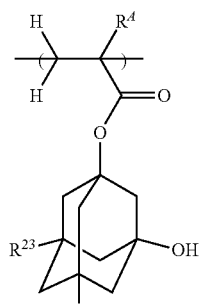
(c)

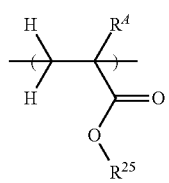
(d)

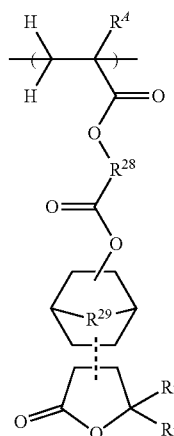
(e)

Herein $R^A$ is each independently hydrogen or methyl, $R^{23}$ and $R^{24}$ are each independently hydrogen or hydroxyl, $R^{25}$ is a substituent group containing a lactone structure, $R^{26}$ and $R^{27}$ are each independently hydrogen or $C_1$-$C_{15}$ alkyl, at least one of $R^{26}$ and $R^{27}$ being $C_1$-$C_{15}$ alkyl, $R^{26}$ and $R^{27}$ may bond together to form a ring with the carbon atom to which they are attached, a combination of $R^{26}$ and $R^{27}$ being a $C_2$-$C_{15}$ alkanediyl group, $R^{28}$ is a $C_1$-$C_{20}$ divalent hydrocarbon group in which any constituent —$CH_2$— may be replaced by —O— or —C(O)—. $R^{29}$ is —CH—, —$CH_2$, —$CH_2CH_2$— or —O—, or two separate —H, and the dotted line designates a single bond or divalent organic group between the norbornane ring, bicyclo[2.2.2]octane ring, 7-oxanorbornane ring or cyclohexane ring structure and the γ-butyrolactone ring structure, or a structure sharing one or two constituent carbon atoms between these ring structures.

The resist composition may further comprise 0.8 to 20.0 parts by weight of a third onium salt having the formula (3).

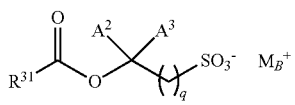

(3)

Herein $A^2$ and $A^3$ are each independently hydrogen or trifluoromethyl, q is an integer of 1 to 3, $M_B^+$ is a sulfonium, iodonium or ammonium cation, and $R^{31}$ is a $C_1$-$C_{40}$ monovalent hydrocarbon group which may contain a heteroatom.

The resist composition may further comprise a compound having the formula (4).

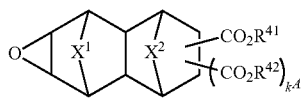

(4)

Herein $X^1$ and $X^2$ are each independently —$CH_2$— or —O—, $k^A$ is 0 or 1, $R^{41}$ and $R^{42}$ are each independently a $C_4$-$C_{20}$ tertiary hydrocarbon group or a group selected from the following.

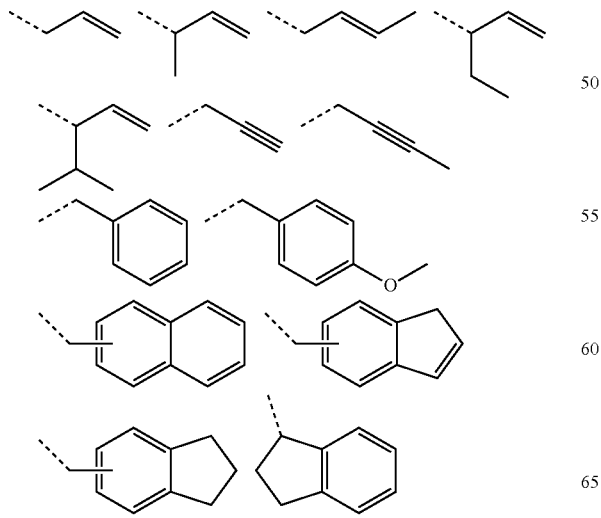

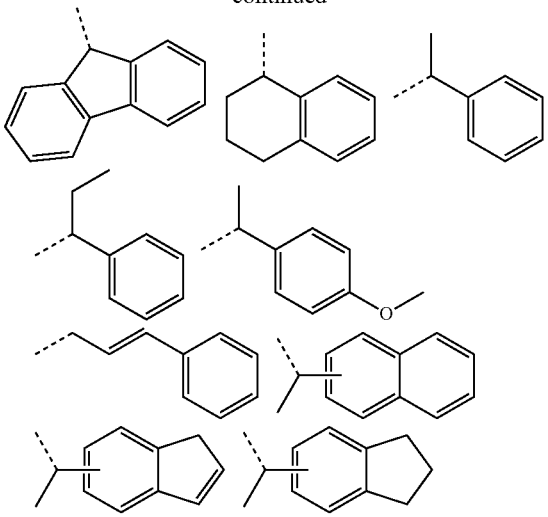

The resist composition may further comprise a fluorinated polymer comprising recurring units of at least one type selected from recurring units having the formulae (f1), (f2) and (f3).

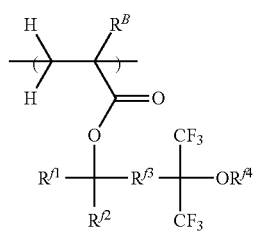

(f1)

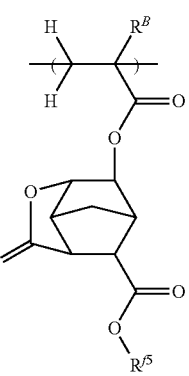

(f2)

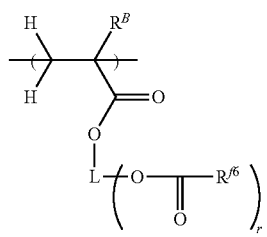

(f3)

Herein $R^B$ is each independently hydrogen, fluorine, methyl or trifluoromethyl, $R^{f1}$ and $R^{f2}$ are each independently hydrogen or a $C_1$-$C_{10}$ monovalent hydrocarbon group, $R^{f3}$ is a single bond or a $C_1$-$C_5$ straight or branched divalent hydrocarbon group, $R^{f4}$ is hydrogen, a $C_1$-$C_{15}$ monovalent hydrocarbon group, $C_1$-$C_{15}$ monovalent fluorinated hydrocarbon group, or acid labile group, with the proviso that when $R^{f4}$ is a monovalent hydrocarbon group or monovalent fluorinated hydrocarbon group, an ether bond or carbonyl moiety may intervene in a carbon-carbon bond, $R^{f5}$ and $R^{f6}$ are each independently a $C_1$-$C_{10}$ monovalent fluorinated hydrocarbon group, L is a $C_1$-$C_{15}$ (r+1)-valent hydrocarbon group or $C_1$-$C_{15}$ (r+1)-valent fluorinated hydrocarbon group, and r is an integer of 1 to 3.

In another aspect, the invention provides a pattern forming process comprising the steps of applying the positive resist composition defined above to form a resist film on a substrate, exposing the resist film to KrF excimer laser, ArF excimer laser, EB or EUV, and developing the exposed resist film in a developer.

In a preferred embodiment, the exposing step is carried out by immersion lithography while a liquid having a refractive index of at least 1.0 is held between the resist film and a projection lens. The pattern forming process may further comprise the step of forming a protective film on the resist film, wherein immersion lithography is carried out while the liquid is held between the protective film and the projection lens.

Advantageous Effects of Invention

The positive resist composition has excellent PED stability and improved DOF performance. A resist pattern having reduced LWR, good profile with controlled footing, and minimal defectivity is formed. The positive resist composition is especially useful in the immersion lithography where a resist film overlaid with a water-repellent protective film is exposed to radiation through water.

BRIEF DESCRIPTION OF DRAWINGS

FIG. 1 is a diagram showing the $^1$H-NMR spectrum of Epoxy compound Q-1 in Synthesis Example 1.

DESCRIPTION OF PREFERRED EMBODIMENTS

As used herein, the singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group. In chemical formulae, the broken line designates a valence bond.

The abbreviations and acronyms have the following meaning.
EB: electron beam
EUV: extreme ultraviolet
Mw: weight average molecular weight
Mn: number average molecular weight
Mw/Mn: molecular weight dispersity
GPC: gel permeation chromatography
PEB: post-exposure bake
PED: post-exposure delay
PAG: photoacid generator
LWR: line width roughness
DOF: depth of focus The positive resist composition is defined as comprising (A) a first onium salt, (B) a second onium salt, (C) an acid labile group-containing base polymer, and (D) an organic solvent.

(A) First Onium Salt

Component (A) is a first onium salt having the formula (1).

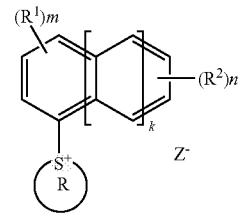

(1)

In formula (1), $R^1$ and $R^2$ each are a hydroxyl group or a $C_1$-$C_{30}$ monovalent hydrocarbon group which may contain a heteroatom. R forms an aliphatic ring of 4 or 5 carbon atoms with $S^+$ in the formula, m and n each are 0 or 1, and k is 0 or 1.

The $C_1$-$C_{30}$ monovalent hydrocarbon group which may contain a heteroatom may be straight, branched or cyclic. Examples thereof include alkyl groups such as methyl, ethyl, propyl, isopropyl, butyl, isobutyl, sec-butyl, tert-butyl, pentyl, neopentyl cyclopentyl, hexyl, heptyl, 2-ethylhexyl, nonyl, undecyl, dodecyl, tridecyl, tetradecyl, pentadecyl, heptadecyl, icosanyl, cyclohexyl, 1-adamantyl, 2-adamantyl, 1-adamantylmethyl, norbornyl, norbornylmethyl, tricyclodecanyl, tetracyclododecanyl, tetracyclododecanylmethyl, and dicyclohexylmethyl, alkenyl groups such as allyl and 3-cyclohexenyl, aryl groups such as phenyl, 1-naphthyl and 2-naphthyl, and aralkyl groups such as benzyl and diphenylmethyl. In these groups, some hydrogen may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl, cyano, carbonyl, ether bond, ester bond, sulfonic acid ester bond, carbonate bond, lactone ring, sultone ring, carboxylic anhydride (—C(=O)—O—C(=O)—) or haloalkyl moiety.

The preferred cations in the onium salts having formula (1) are those having the formulae (1a) to (1d).

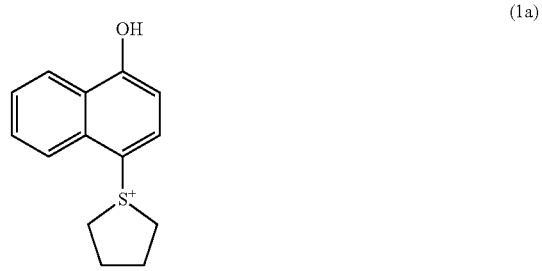

(1a)

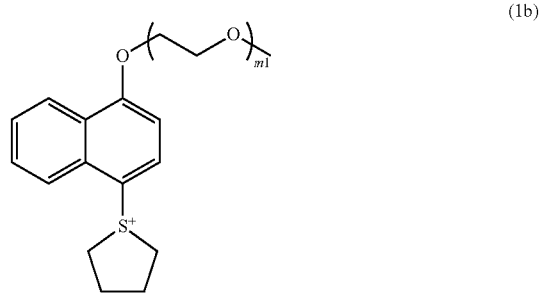

(1b)

-continued

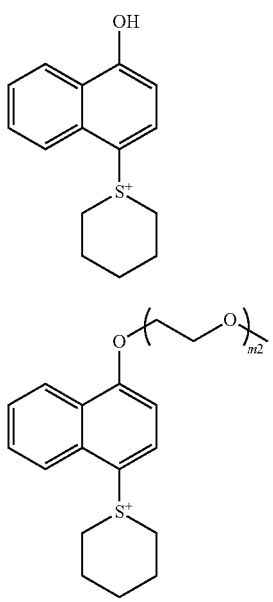

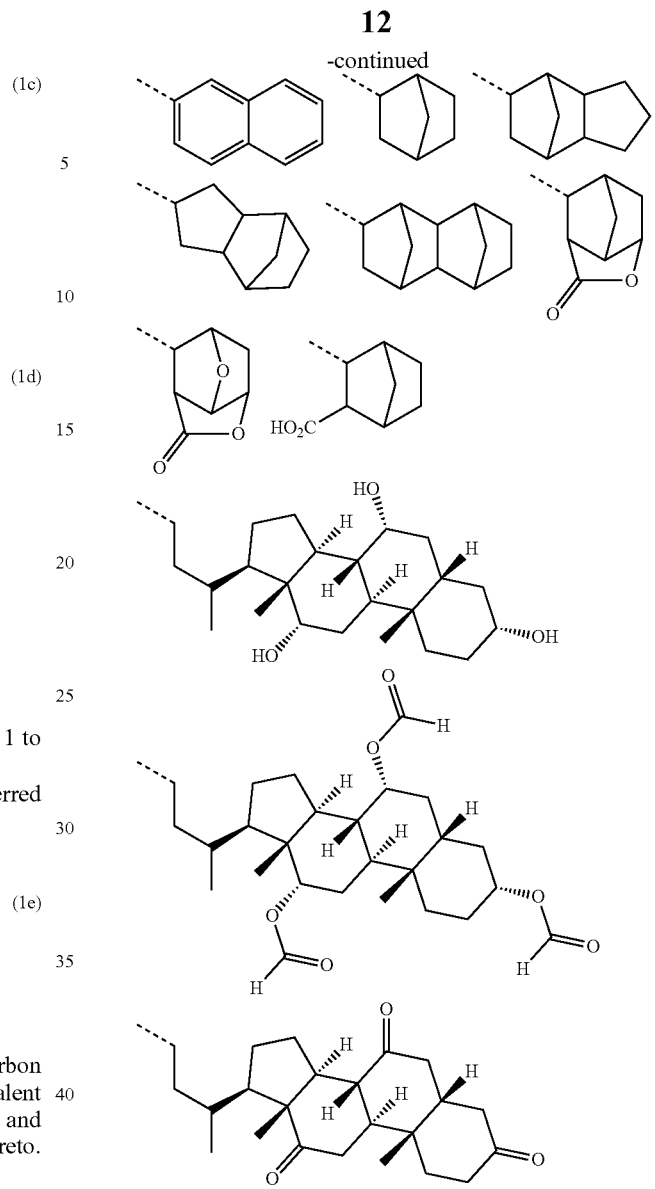

Herein m¹ and m² are each independently an integer of 1 to 4.

In formula (1), $Z^-$ is an organic anion. The preferred organic anion has the formula (1e).

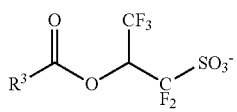

In formula (1e), $R^3$ is a $C_1$-$C_{40}$ monovalent hydrocarbon group which may contain a heteroatom. The monovalent hydrocarbon group may be straight, branched or cyclic and examples thereof are shown below, but not limited thereto.

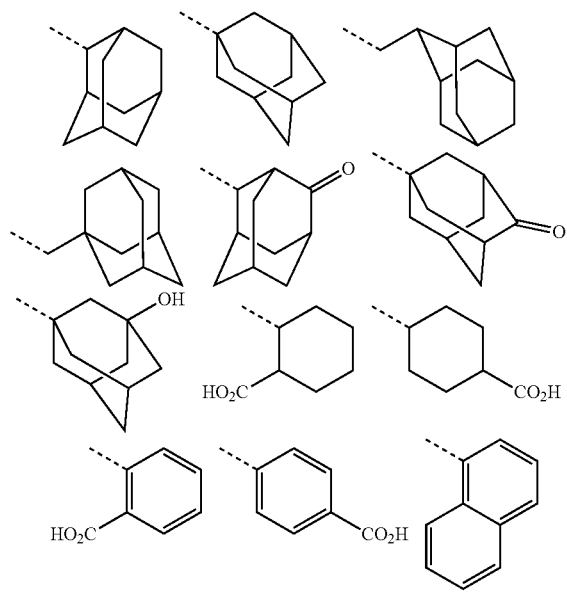

In the positive resist composition, the first onium salt (A) functions as a photoacid generator. As used herein, the photoacid generator refers to a compound which generates an acid in response to actinic ray or radiation, the acid having a sufficient acidity to induce deprotection reaction of acid labile groups on the base polymer.

In the positive resist composition, the first onium salt (A) is present in an amount of 4.1 to 20 parts by weight, preferably 5 to 17 parts by weight per 80 parts by weight of the base polymer (C).

(B) Second Onium Salt

Component (B) is a second onium salt having the formula (2).

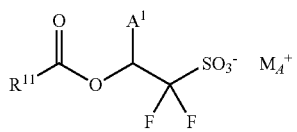

In formula (2), $A^1$ is hydrogen or trifluoromethyl. $R^{11}$ is a nitrogen-containing heterocyclic group or a group having the formula (2-1).

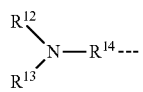
(2-1)

In formula (2-1), $R^{12}$ and $R^{13}$ are each independently hydrogen or a $C_1$-$C_{20}$ monovalent hydrocarbon group which may contain a heteroatom, $R^{12}$ and $R^{13}$ may bond together to form a ring with the nitrogen atom to which they are attached. $R^{14}$ is a $C_1$-$C_{20}$ divalent hydrocarbon group which may contain a heteroatom. The broken line designates a valence bond.

Examples of the nitrogen-containing heterocyclic group $R^{11}$ include monovalent groups derived from aziridine, pyrrolidine, piperidine, morpholine, pyrrole, pyridine, azetidine, oxazole, isooxazole, thiazole, isothiazole, imidazole, pyrazole, pyridazine, pyrimidine, pyrazine, pyrroline, 2-imidazoline, imidazolidine, 3-pyrazoline, pyrazolidine, piperazine, triazine, oxadiazine, dithiazine, indole, isoindole, quinoline, isoquinoline, cinnoline, phthalazine, quinazoline, quinoxaline, 1,8-naphthylidine, purine, pteridine, indolizine, carbazole, acridine, phenazine, phenanthridine, 1,10-phenanthroline, phenoxazine, indoline, isoindoline, quinuclidine, benzo[e]indole, and benzo[cd]indole.

The $C_1$-$C_{20}$ monovalent hydrocarbon groups represented by $R^{12}$ and $R^{13}$ may be straight, branched or cyclic. Examples thereof include alkyl groups such as methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl, alkenyl groups such as vinyl, allyl, propenyl, butenyl, hexenyl and cyclohexenyl, aryl groups such as phenyl and naphthyl, heteroaryl groups such as thienyl, and aralkyl groups such as benzyl, 1-phenylethyl and 2-phenylethyl. In these groups, some hydrogen may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl, cyano, carbonyl, ether bond, ester bond, sulfonic acid ester bond, carbonate moiety, lactone ring, sultone ring, carboxylic anhydride or haloalkyl moiety.

When $R^{12}$ and $R^{13}$ bond together to form a ring with the nitrogen atom to which they are attached, examples of the ring include aziridine, pyrolidine, piperidine, morpholine, pyrrole, pyridine, azetidine, oxazole, isooxazole, thiazole, isothiazole, imidazole, pyrazole, pyridazine, pyrimidine, pyrazine, pyrroline, 2-imidazoline, imidazolidine, 3-pyrazoline, pyrazolidine, piperazine, triazine, oxadiazine, dithiazine, indole, isoindole, quinoline, isoquinoline, cinnoline, phthalazine, quinazoline, quinoxaline, 1,8-naphthylidine, purine, pteridine, indolizine, carbazole, acridine, phenazine, phenanthridine, 1,10-phenanthroline, phenoxazine, indoline, isoindoline, quinuclidine, benzo[e]indole, and benzo[cd]indole. In these rings, some hydrogen may be substituted by a monovalent hydrocarbon group as exemplified above or a moiety containing a heteroatom such as oxygen, sulfur, nitrogen or halogen, or some carbon may be replaced by a moiety containing a heteroatom such as oxygen, sulfur or nitrogen, so that the ring may contain a hydroxyl, cyano, carbonyl, ether bond, ester bond, sulfonic acid ester bond, carbonate moiety, lactone ring, sultone ring, carboxylic anhydride or haloalkyl moiety.

The divalent hydrocarbon groups represented by $R^{14}$ include straight alkanediyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, and heptadecane-1,117-diyl; branched alkanediyl groups which are the foregoing straight alkanediyl groups having methyl, ethyl, propyl, isopropyl, butyl, sec-butyl, and tert-butyl pendants; cyclic alkanediyl groups such as cyclopentanediyl, cyclohexanediyl, norbornanediyl, and adamantanediyl; and arylene groups such as phenylene and naphthylene. Also included are the foregoing groups in which some hydrogen is substituted by a moiety containing a heteroatom such as oxygen, sulfur, nitrogen or halogen, or some carbon is replaced by a moiety containing a heteroatom such as oxygen, sulfur or nitrogen, so that the group may contain a hydroxyl, cyano, carbonyl, ether bond, ester bond, sulfonic acid ester bond, carbonate bond, lactone ring, sultone ring, carboxylic anhydride or haloalkyl moiety.

Examples of the anion in the onium salt having formula (2) are shown below, but not limited thereto.

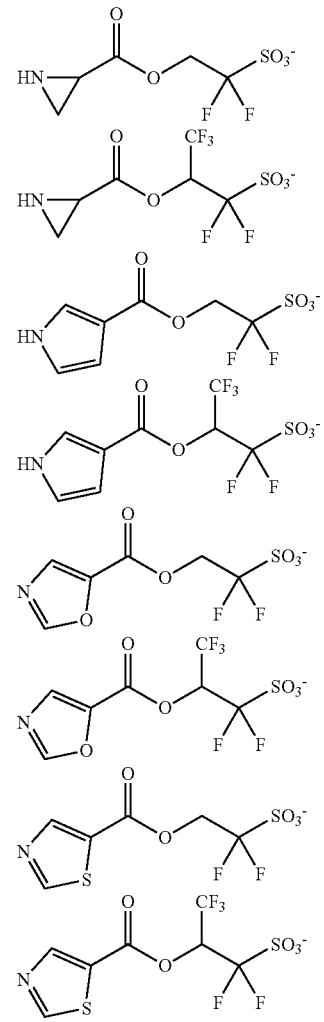

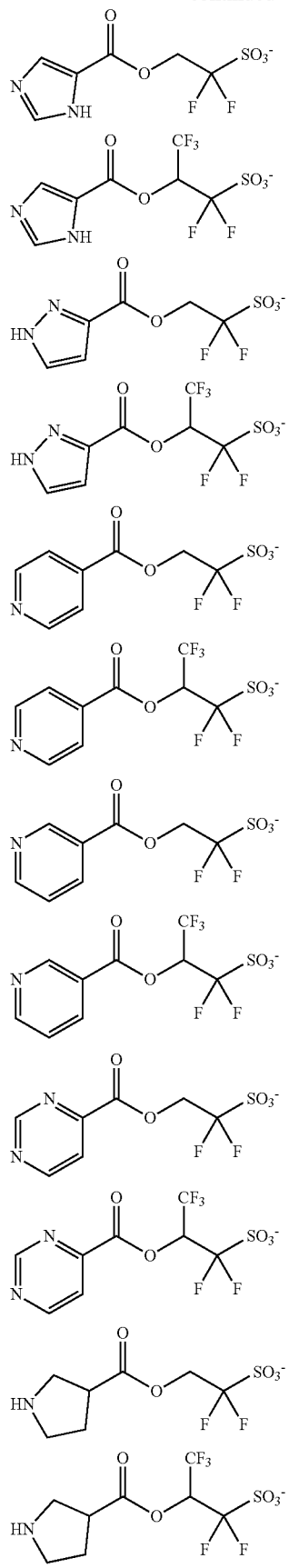
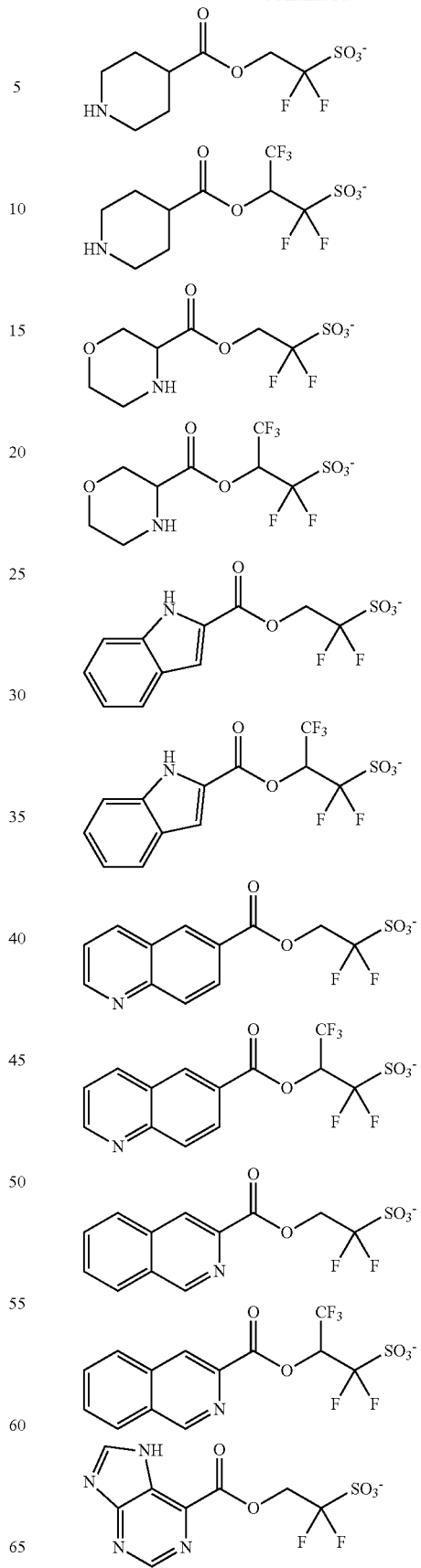

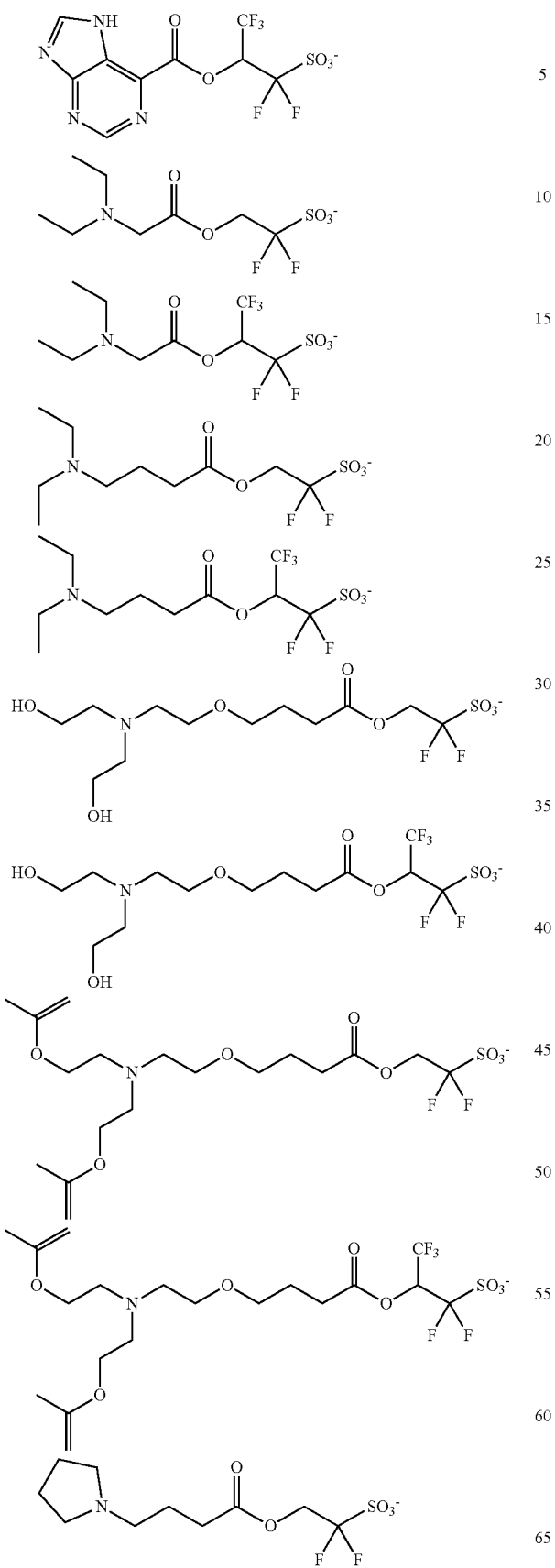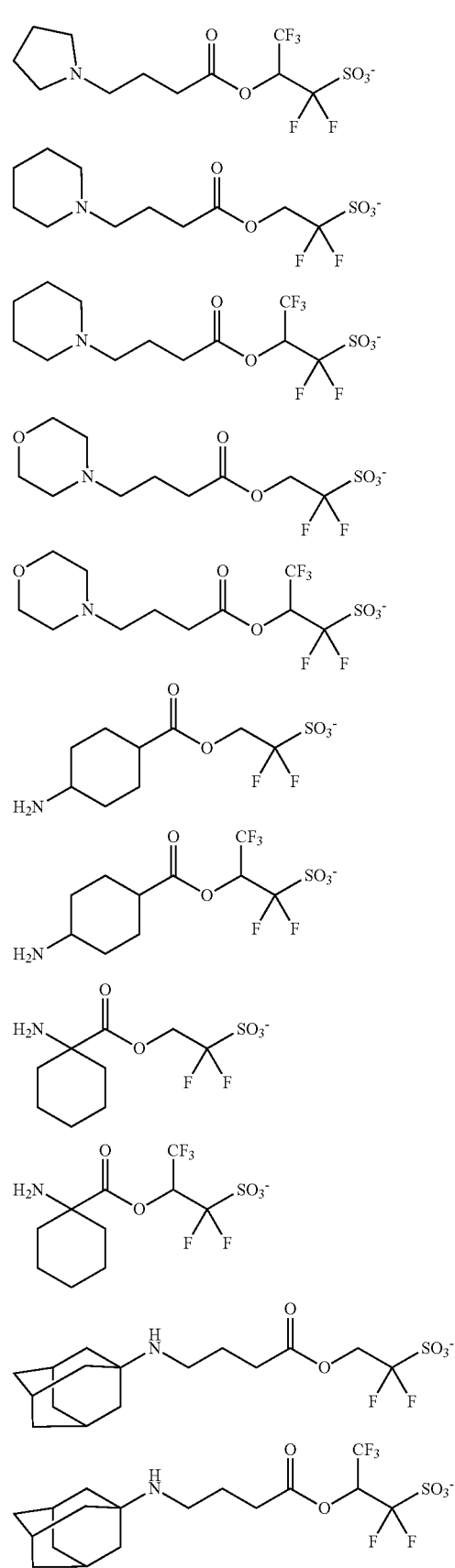

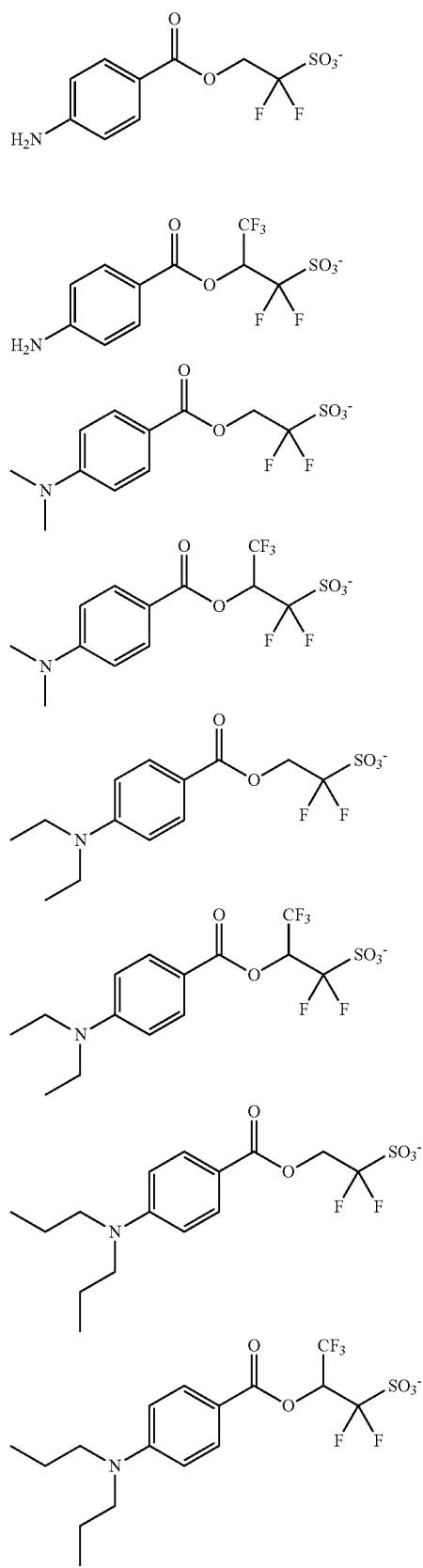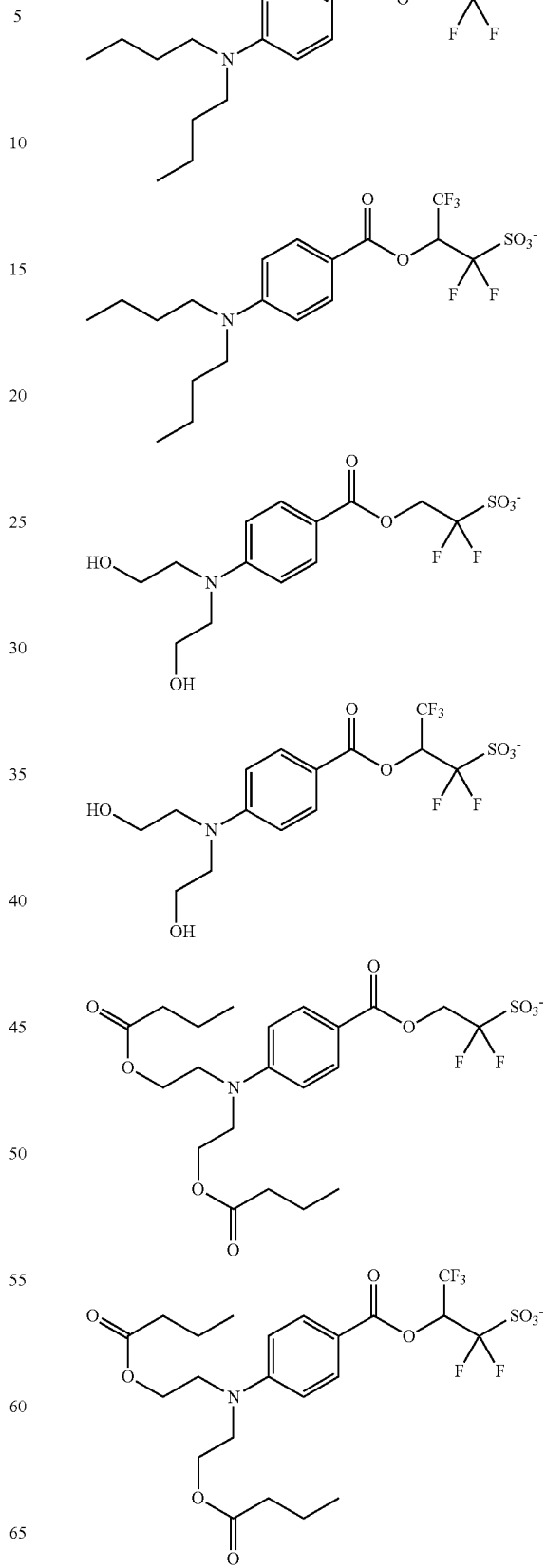

-continued

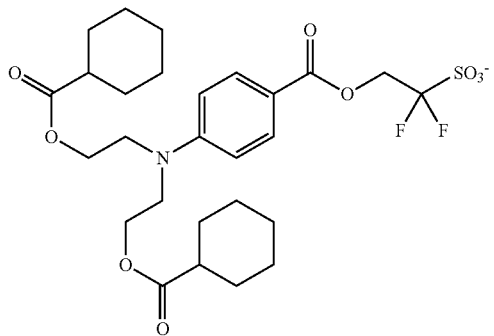
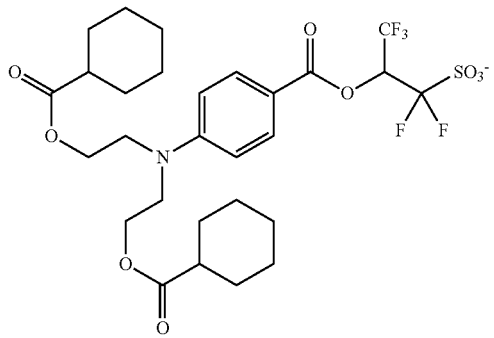
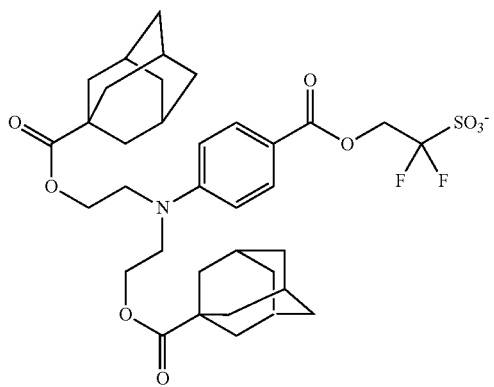
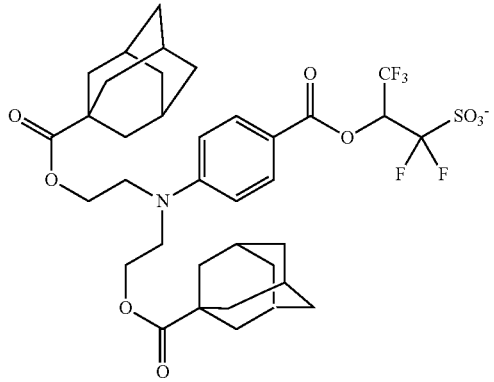
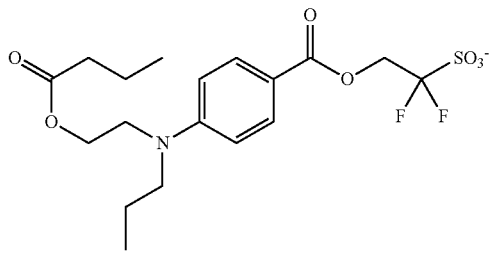

-continued

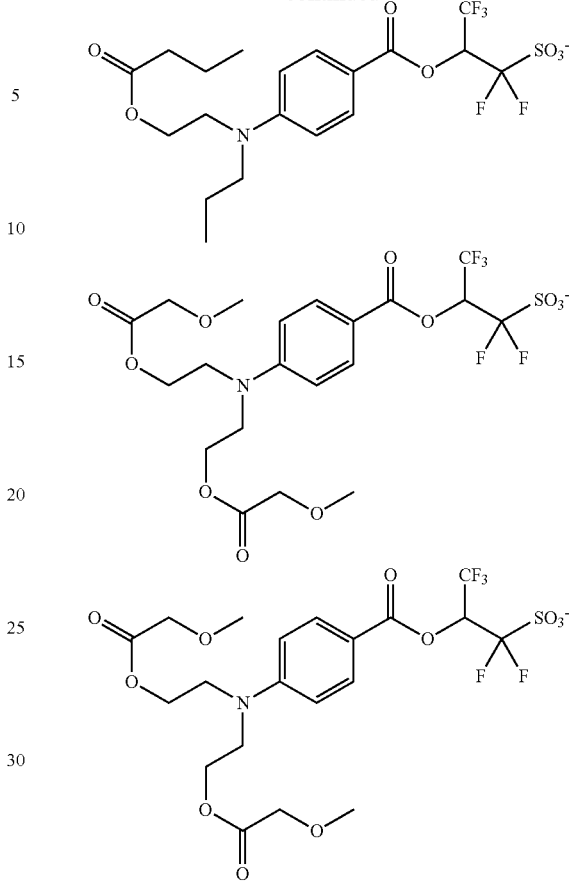

In formula (2), $M_A^+$ is a sulfonium cation having the formula (2A) or an iodonium cation having the formula (2B).

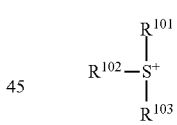

(2A)

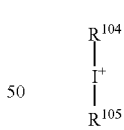

(2B)

In formulae (2A) and (2B), $R^{101}$, $R^{102}$, $R^{103}$, $R^{104}$ and $R^{105}$ are each independently a $C_1$-$C_{20}$ monovalent hydrocarbon group which may contain a heteroatom. Any two or more of $R^{101}$, $R^{102}$ and $R^{103}$ may bond together to form a ring with the sulfur atom to which they are attached. The $C_1$-$C_{20}$ monovalent hydrocarbon group may be straight, branched or cyclic. Examples thereof include alkyl groups such as methyl, ethyl, n-propyl, isopropyl, n-butyl, tert-butyl, cyclopropyl, cyclopentyl, cyclohexyl, cyclopropylmethyl, 4-methylcyclohexyl, cyclohexylmethyl, norbornyl, and adamantyl, alkenyl groups such as vinyl, allyl, propenyl, butenyl, hexenyl and cyclohexenyl, aryl groups such as phenyl and naphthyl, heteroaryl groups such as thienyl, and aralkyl groups such as benzyl, 1-phenylethyl and 2-phenylethyl, with the aryl groups being preferred. In these groups, some hydrogen may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl, cyano, carbonyl, ether bond, ester bond, sulfonic acid ester bond, carbonate moiety, lactone ring, sultone ring, carboxylic anhydride or haloalkyl moiety.

Examples of the sulfonium cation having formula (2A) are shown below, but not limited thereto.

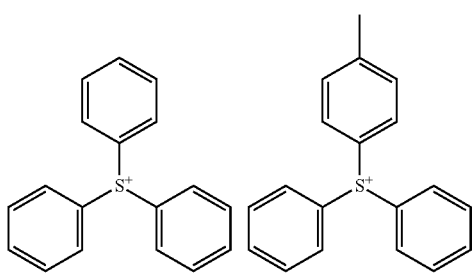
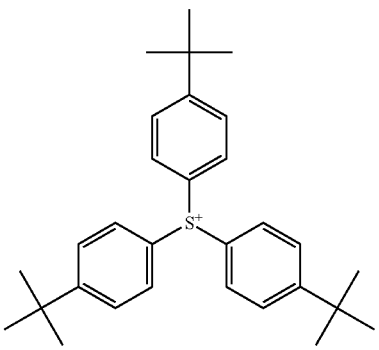
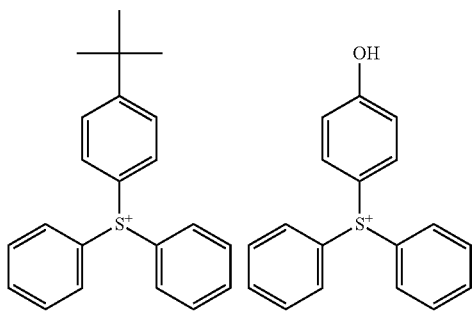
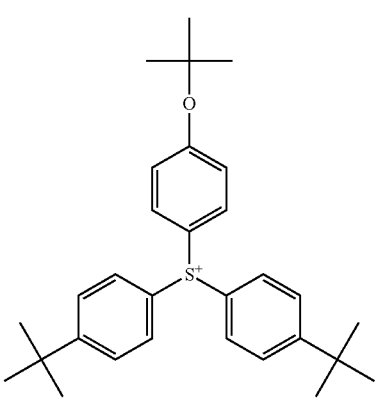
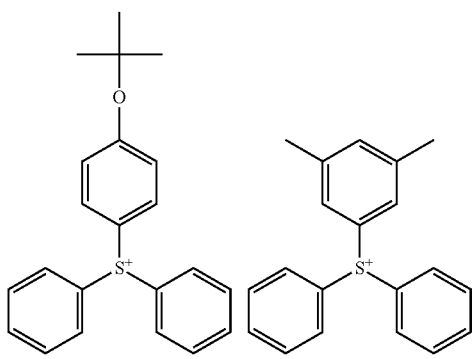
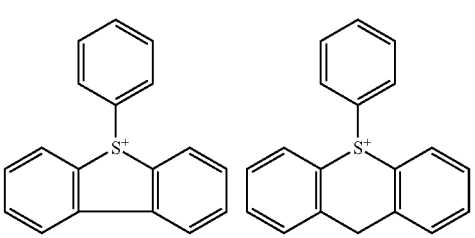
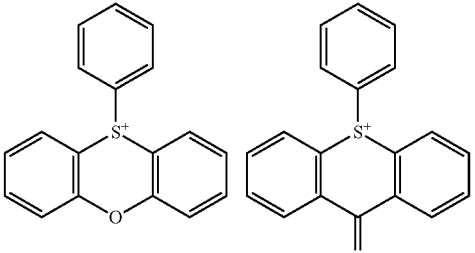
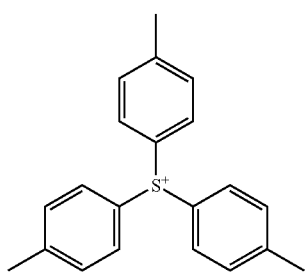
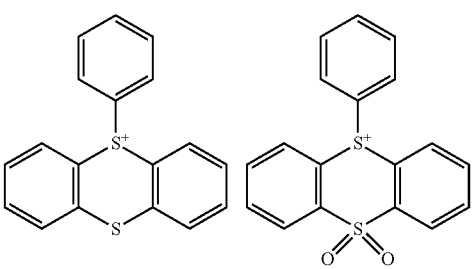
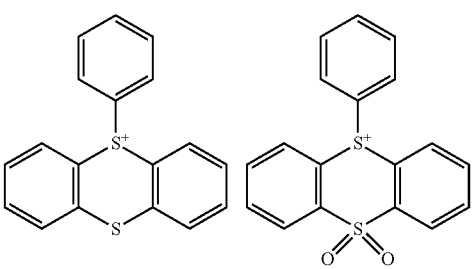

-continued

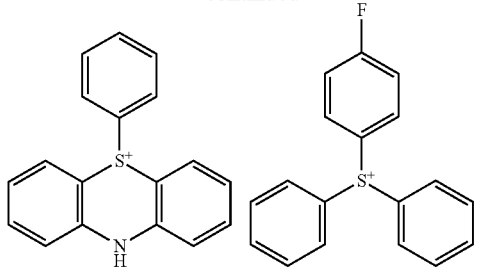

Examples of the iodonium cation having formula (2B) include bis(4-methylphenyl)iodonium, bis(4-ethylphenyl)iodonium, bis(4-tert-butylphenyl)iodonium, bis(4-(1,1-dimethylpropyl)phenyl)iodonium, bis(4-methoxyphenyl)iodonium, (4-methoxyphenyl)phenyl)phenyliodonium, (4-tert-butoxyphenyl)phenyliodonium, (4-acryloyloxyphenyl)phenyliodonium, and (4-methacyloyloxyphenyl)phenyliodonium. Inter alia, bis(4-tert-butylphenyl)iodonium is preferred.

In the positive resist composition, the second onium salt (B) functions as a quencher or acid diffusion inhibitor. As used herein, the "quencher" refers to a compound which traps an acid generated by a PAG in the resist composition to prevent the acid from diffusing into the unexposed region.

In the positive resist composition, the second onium salt (B) is present in an amount of 2.3 to 8.8 parts by weight, preferably 3 to 7 parts by weight per 80 parts by weight of the base polymer (C). The second onium salt may be used alone or in admixture of two or more.

(C) Base Polymer

Component (C) is an acid labile group-containing base polymer, specifically a polymer comprising recurring units having the formula (a), also referred to as recurring units (a), hereinafter.

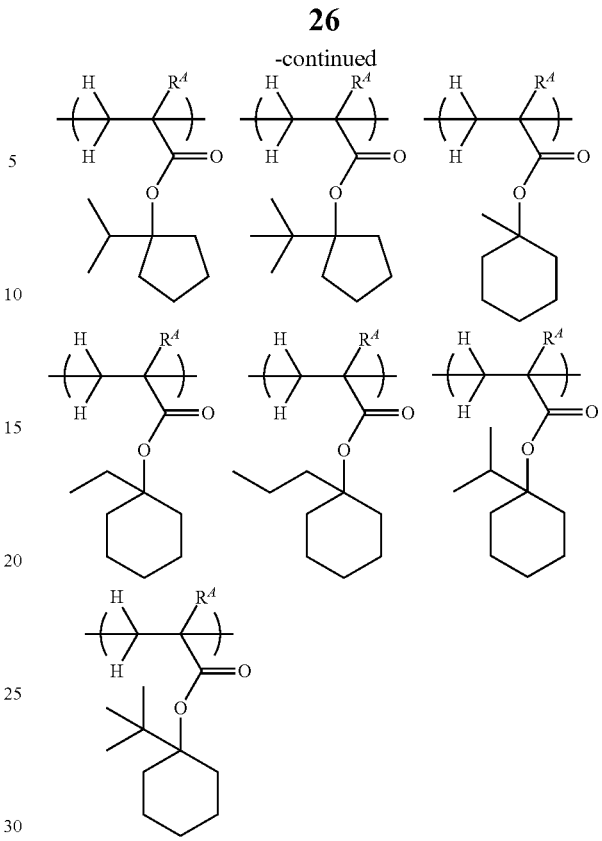

The base polymer may further comprise recurring units having the formula (b) as the acid labile group-containing unit. The recurring units having the formula (b) are also referred to as recurring units (b), hereinafter.

(a)

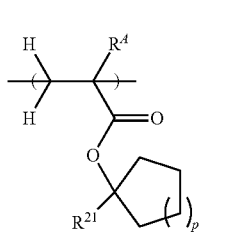

In formula (a), $R^4$ is hydrogen or methyl, preferably methyl. $R^{21}$ is a $C_1$-$C_8$ straight or branched alkyl group. Exemplary of the alkyl group are methyl, ethyl, n-propyl, isopropyl, n-butyl, isobutyl, sec-butyl, and tert-butyl.

In formula (a), p is an integer of 1 to 3, preferably 1 or 2.

Examples of the recurring unit (a) are shown below, but not limited thereto. Herein $R^4$ is as defined above.

(b)

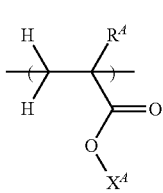

In formula (b), $R^4$ is hydrogen or methyl. $X^4$ is an acid labile group other than the group having the formula (b1):

(b1)

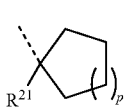

wherein $R^{21}$ and p are as defined above.

The acid labile group represented by $X^4$ is preferably of 13 or less carbon atoms. A carbon count of up to 13 is preferred because the desired DOF is achievable. When recurring units (b) are included, it is acceptable that those recurring units containing an acid labile group ($X^4$) of at least 14 carbon atoms be included in an amount of up to 5 mol % of the overall recurring units.

The acid labile group $X^4$ is preferably selected from groups having the formulae (L1) to (L3), but not limited thereto.

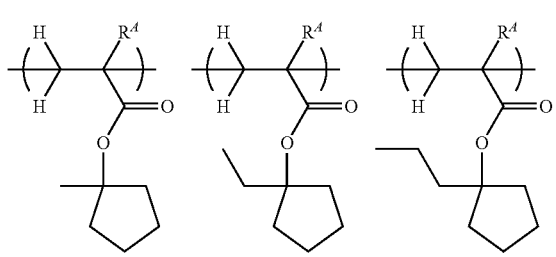

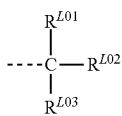
(L1)

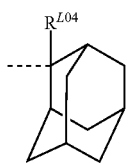
(L2)

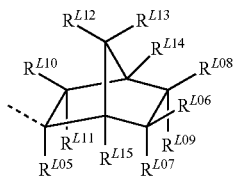
(L3)

In formula (L1), $R^{L01}$ to $R^{L03}$ are each independently hydrogen or a $C_1$-$C_{12}$ alkyl group. The alkyl group may be straight, branched or cyclic and examples thereof include methyl, ethyl, propyl, isopropyl, n-butyl, sec-butyl, tert-butyl, cyclopentyl, cyclohexyl, 2-ethylhexyl, n-octyl, 1-adamantyl, and 2-adamantyl. The group having formula (L1) is preferably of 13 or less carbon atoms.

Examples of the acid labile group having formula (L1) include tert-butyl, tert-pentyl and the groups shown below, but are not limited thereto.

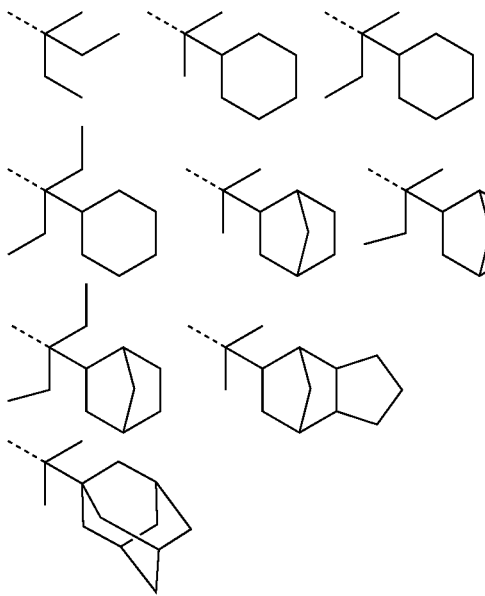

In formula (L2), $R^{L04}$ is hydrogen or a $C_1$-$C_3$ straight or branched alkyl group. Suitable alkyl groups include methyl, ethyl, propyl and isopropyl. The group having formula (L2) is preferably of 13 or less carbon atoms.

Examples of the acid labile group having formula (L2) are shown below, but not limited thereto.

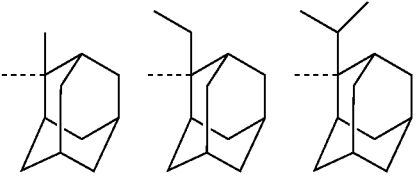

In formula (L3), $R^{L05}$ to $R^{L15}$ are each independently hydrogen or a $C_1$-$C_6$ monovalent hydrocarbon group. The monovalent hydrocarbon group may be straight, branched or cyclic and examples thereof include straight, branched or cyclic alkyl groups such as methyl, ethyl, propyl, isopropyl, n-butyl, sec-butyl, tert-butyl, tert-pentyl, n-pentyl, n-hexyl, cyclopentyl, and cyclohexyl. Any two of $R^{L06}$ to $R^{L15}$ (e.g., $R^{L06}$ and $R^{L07}$, $R^{L06}$ and $R^{L08}$, $R^{L07}$ and $R^{L09}$, $R^{L08}$ and $R^{L09}$, $R^{L10}$ and $R^{L11}$, $R^{L12}$ and $R^{L13}$) may bond together to form a ring. The group having formula (L3) is preferably of 13 or less carbon atoms.

Examples of the acid labile group having formula (L3) are shown below, but not limited thereto.

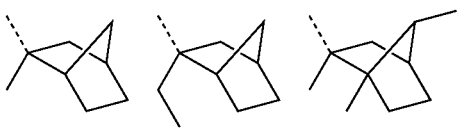

In the base polymer, the acid labile group-containing units, that is, recurring units (a) and (b) are preferably incorporated in an amount of 25 to 70 mol %, more preferably 40 to 60 mol % of the overall recurring units. Specifically, recurring units (a) are preferably incorporated in an amount of at least 50 mol %, more preferably at least 80 mol % of the acid labile group-containing units, while recurring units (b) are preferably incorporated in an amount of up to 50 mol %, more preferably up to 20 mol % of the acid labile group-containing units.

The base polymer may further comprise recurring units of at least one type selected from recurring units having the formula (c), recurring units having the formula (d), and recurring units having the formula (e). These units are also referred to as recurring units (c), (d) and (e), hereinafter.

(c)

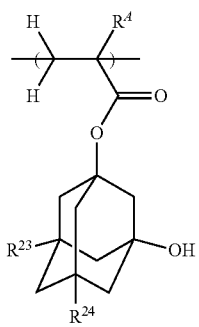

(d)

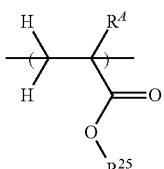

(e)

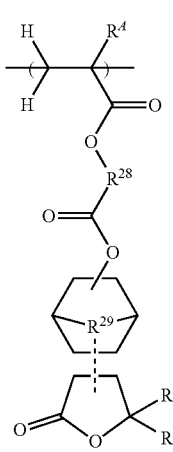

In formulae (c) to (e). $R^A$ is each independently hydrogen or methyl. $R^{23}$ and $R^{24}$ are each independently hydrogen or hydroxyl. $R^{25}$ is a substituent group containing a lactone structure. $R^{26}$ and $R^{27}$ are each independently hydrogen or $C_1$-$C_{15}$ alkyl, at least one of $R^{26}$ and $R^{27}$ being $C_1$-$C_{15}$ alkyl. $R^{26}$ and $R^{27}$ may bond together to form a ring with the carbon atom to which they are attached, a combination of $R^{26}$ and $R^{27}$ being a $C_2$-$C_{15}$ alkanediyl group. $R^{28}$ is a $C_1$-$C_{20}$ divalent hydrocarbon group in which any constituent —$CH_2$— may be replaced by —O— or —C(=O)—. $R^{29}$ is —$CH_2$—, —$CH_2CH_2$— or —O—, or two separate —H, and the dotted line designates a single bond or divalent organic group between the norbornane ring, bicyclo[2.2.2]octane ring, 7-oxanorbornane ring or cyclohexane ring structure and the γ-butyrolactone ring structure, or a structure sharing one or two constituent carbon atoms between these ring structures.

The $C_1$-$C_{20}$ divalent hydrocarbon group represented by $R^{28}$ may be straight, branched or cyclic, and examples thereof are shown below, but not limited thereto.

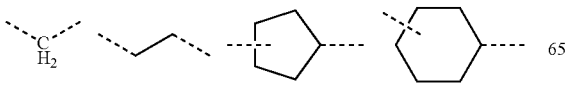

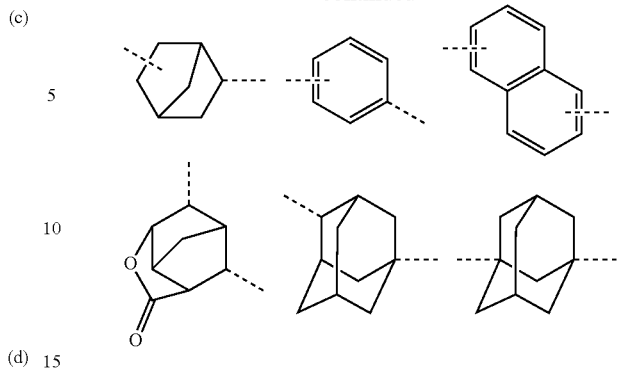

The $C_1$-$C_{15}$ alkyl groups represented by $R^{26}$ and $R^{27}$ may be straight, branched or cyclic, and examples thereof include methyl, ethyl, n-propyl, isopropyl, cyclopropyl, n-butyl, isobutyl, sec-butyl, tert-butyl, cyclobutyl, n-pentyl, cyclopentyl, n-hexyl, cyclohexyl, n-heptyl, n-octyl, n-nonyl, n-decyl, n-undecyl, n-dodecyl, tridecyl, tetradecyl, pentadecyl, adamantyl, and norbornyl. Inter alia, $C_6$-$C_6$ alkyl groups are preferred.

In formula (e), $R^{29}$ is —$CH_2$—, —$CH_2CH_2$— or —O—, or two separate —H. When $R^{29}$ is —$CH_2$—, a norbornane ring structure is formed. When $R^{29}$ is —$CH_2CH_2$—, a bicyclo[2.2.2]octane ring structure is formed. When $R^{29}$ is —O—, a 7-oxanorbornane ring structure is formed. When $R^{29}$ is two separate —H, a cyclohexane ring structure is formed as shown below.

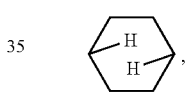

that is,

Examples of the divalent organic group represented by the dotted line in formula (e) include $C_1$-$C_6$ alkanediyl groups and $C_1$-$C_5$ oxaalkanediyl groups.

Preferred examples of the recurring unit (c) are shown below, but not limited thereto. Herein $R^A$ is as defined above.

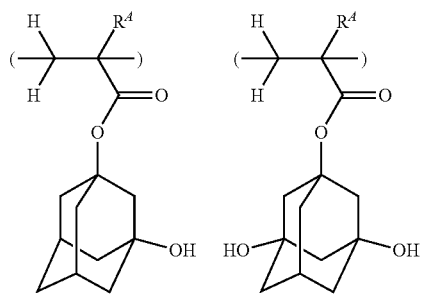

Preferred examples of the recurring unit (d) are shown below, but not limited thereto. Herein $R^A$ is as defined above.

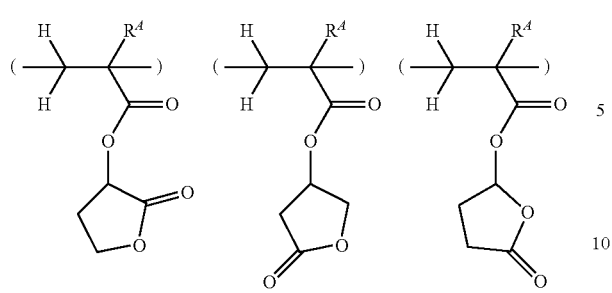
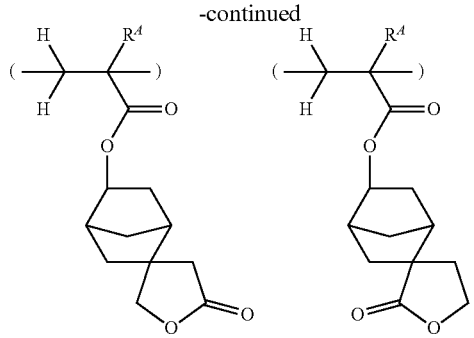
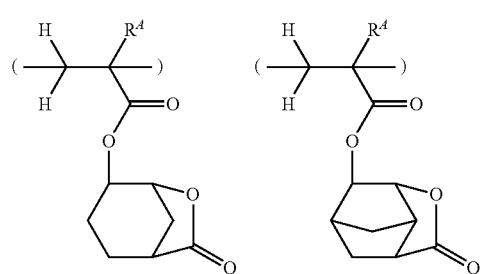
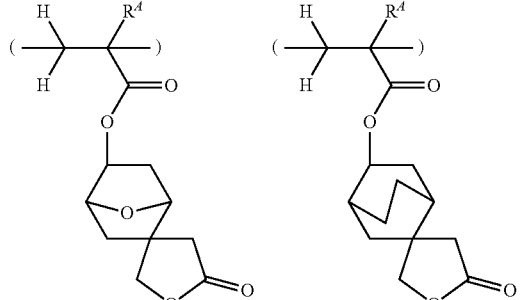
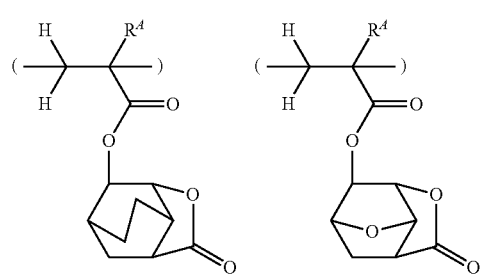
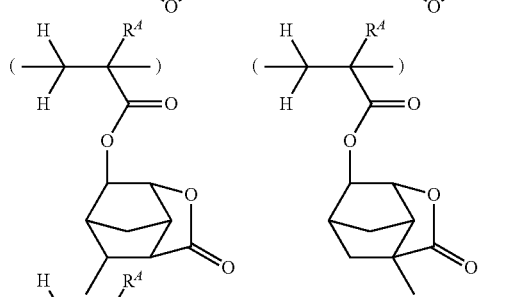
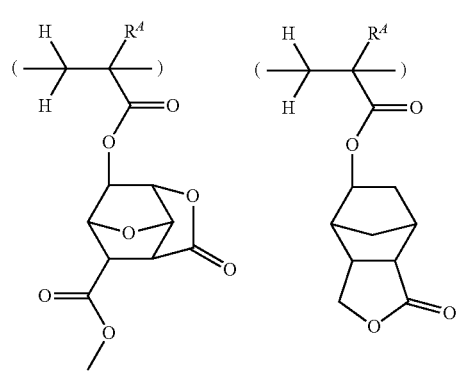
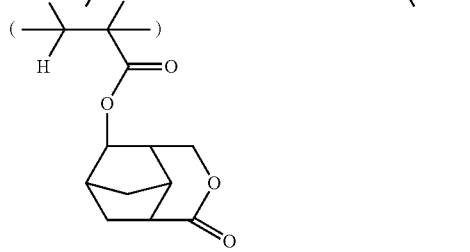
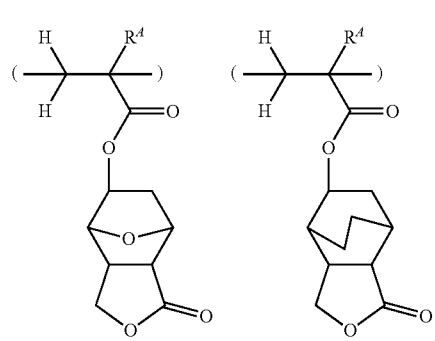
Preferred examples of the recurring unit (e) are shown below, but not limited thereto. Herein $R^A$ is as defined above.
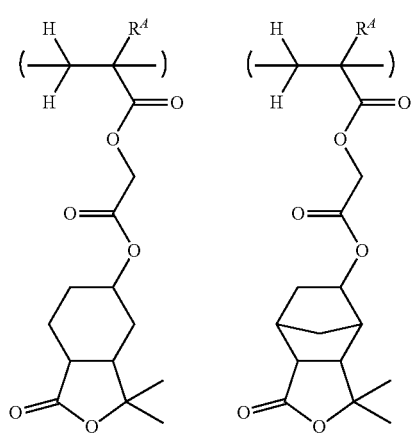

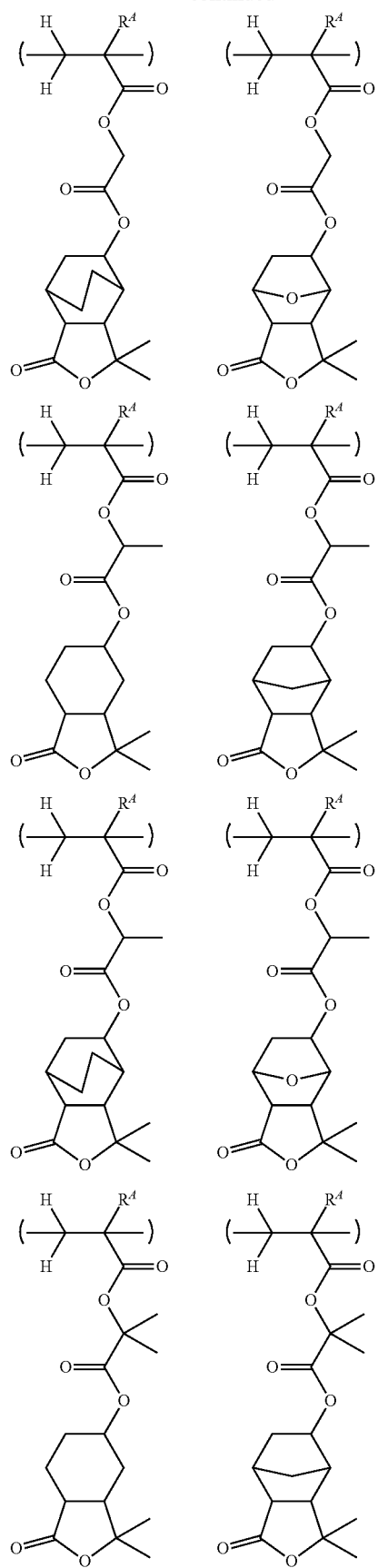
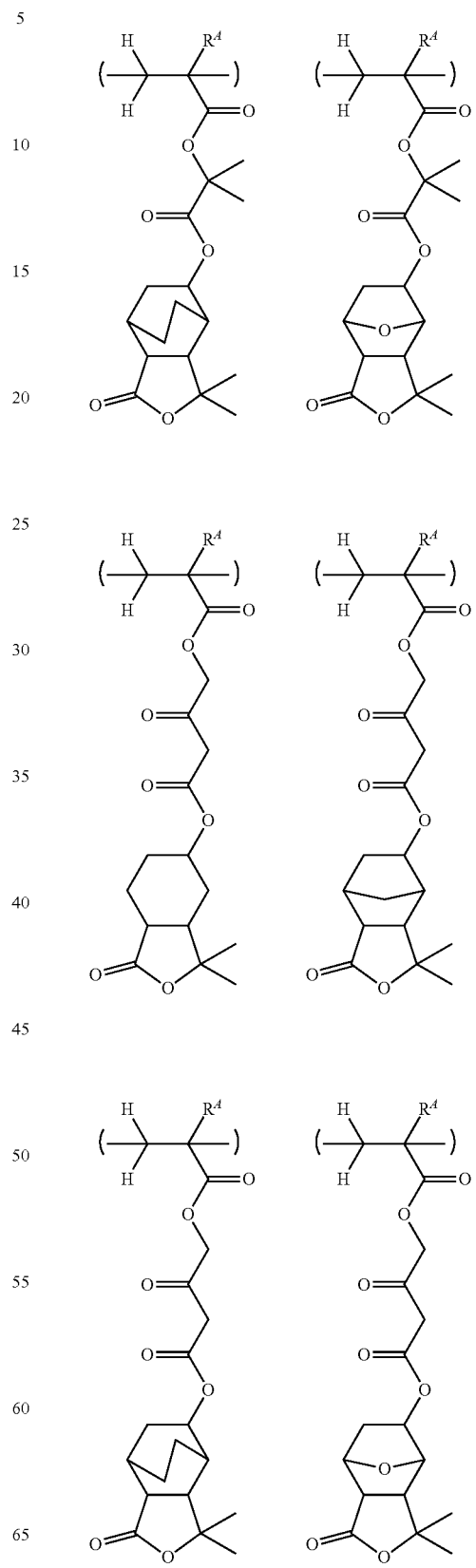

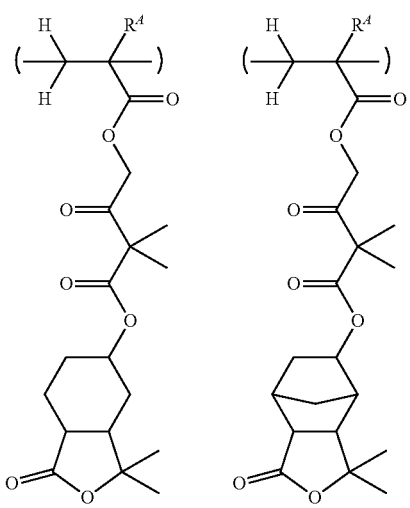
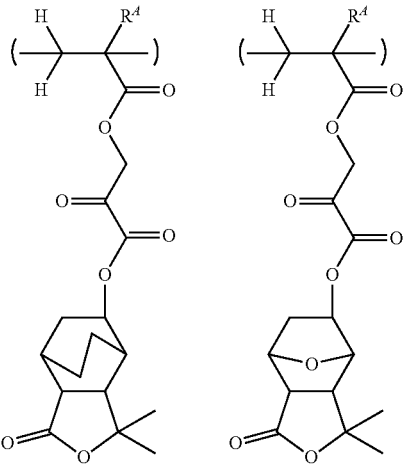
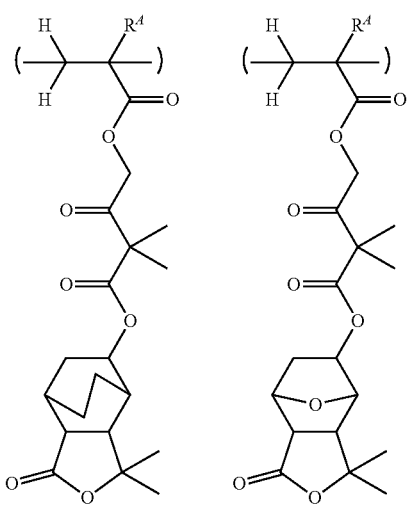
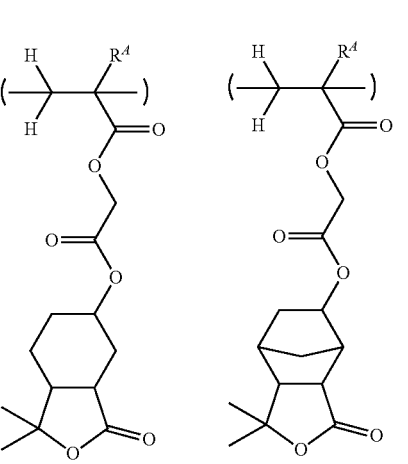
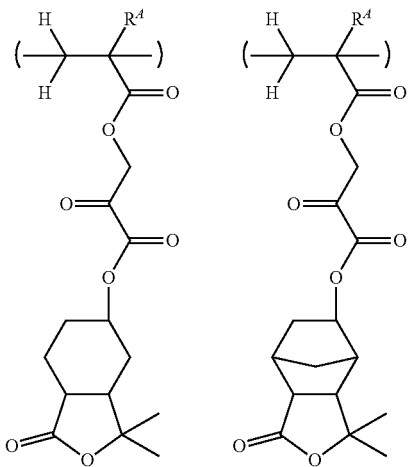
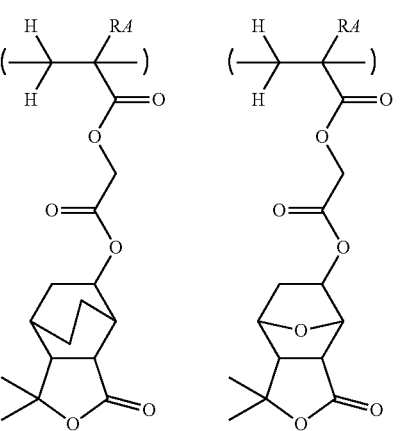

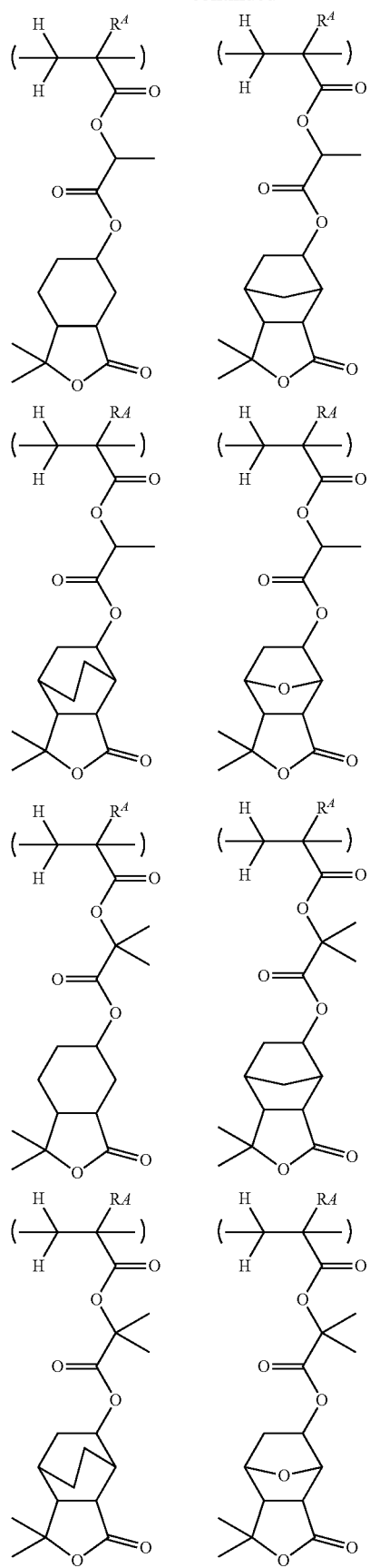
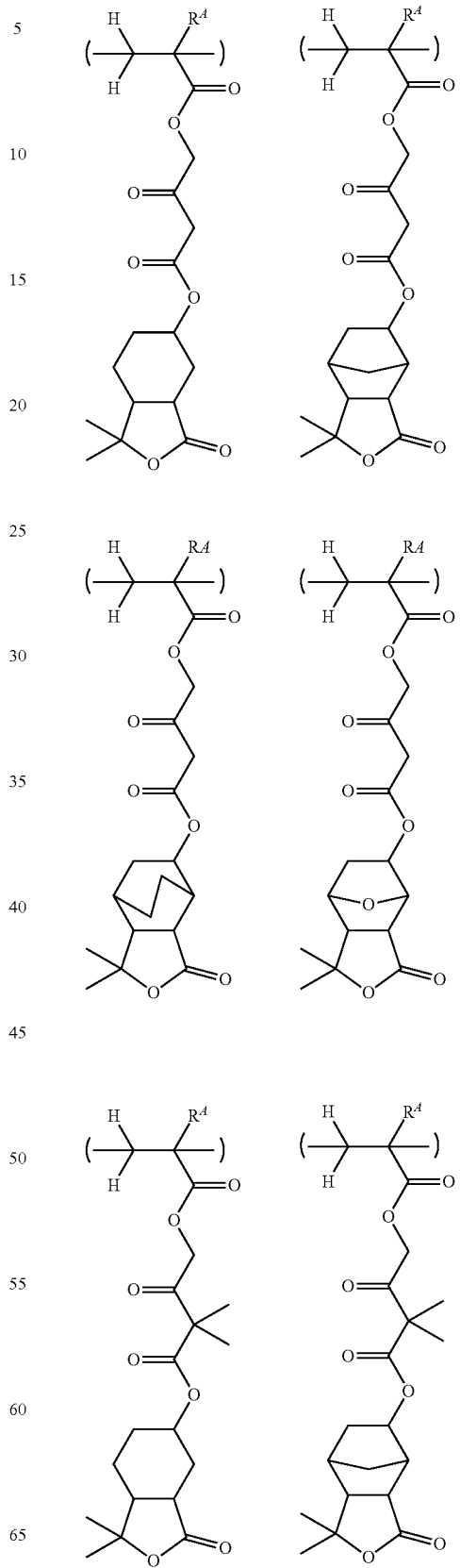

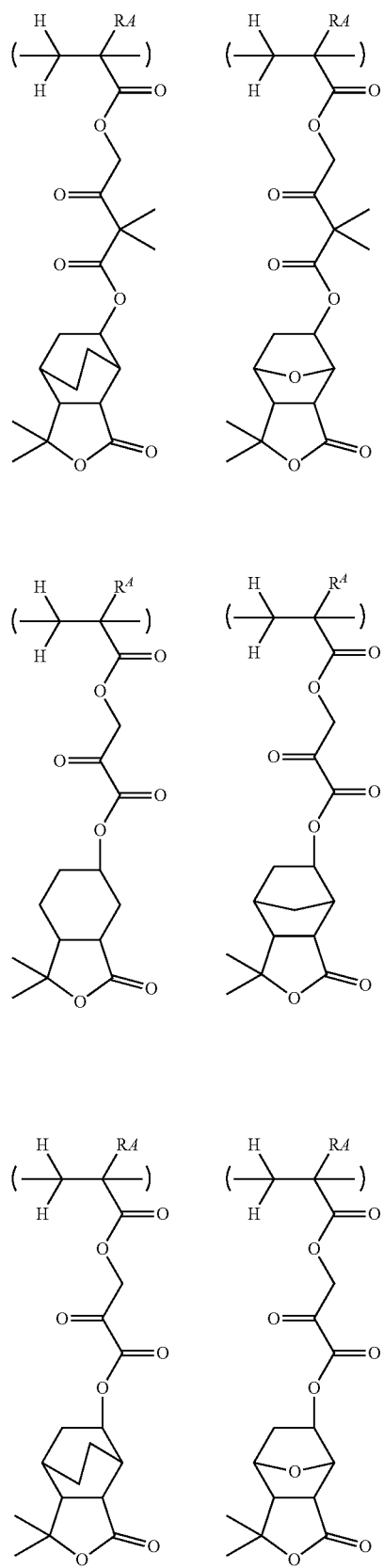
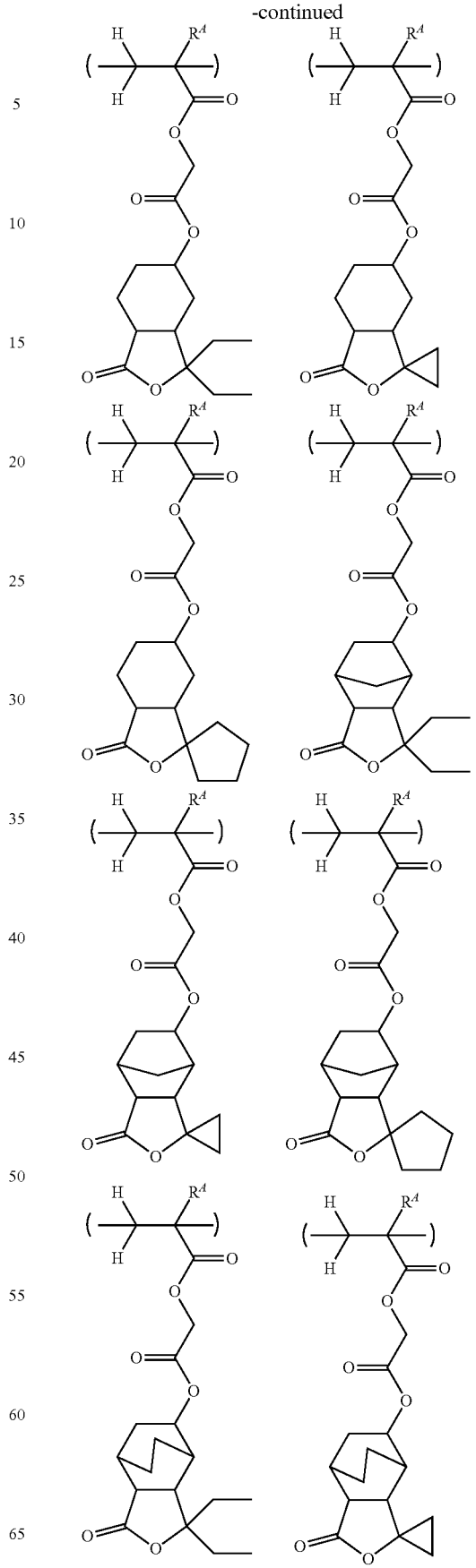

-continued
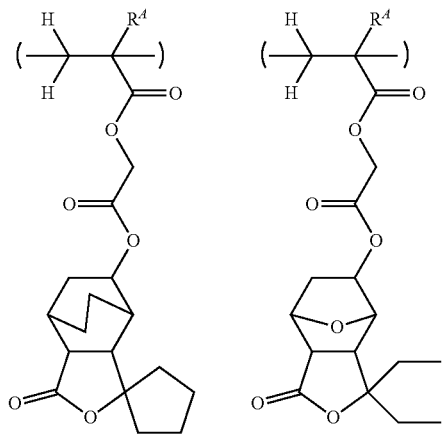
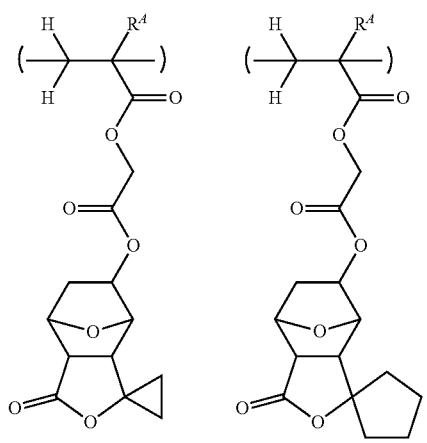
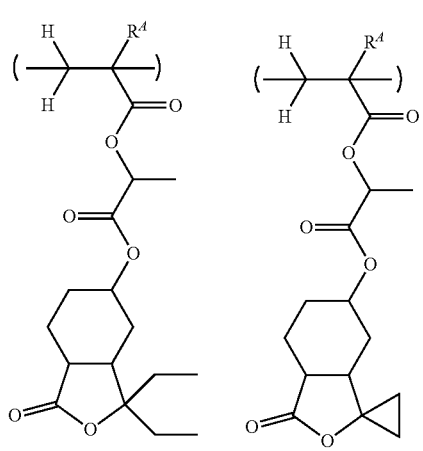
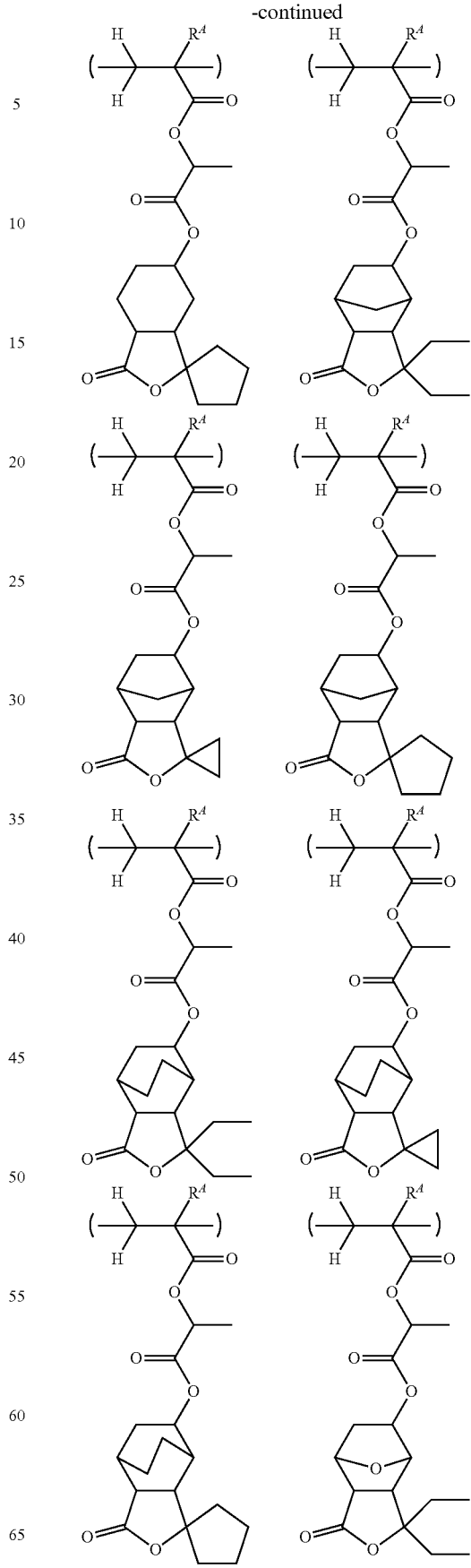

-continued

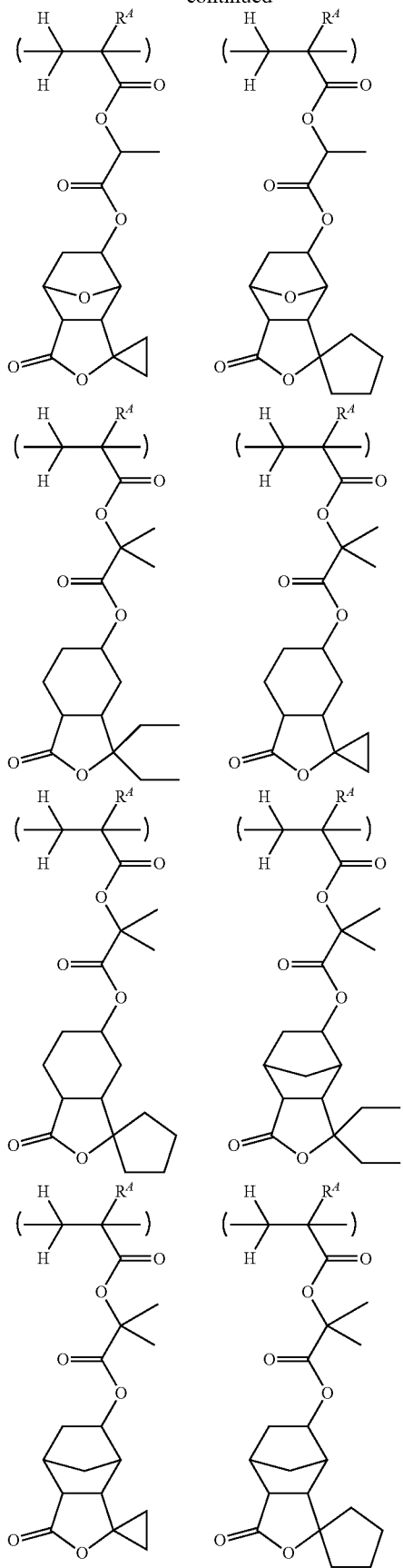

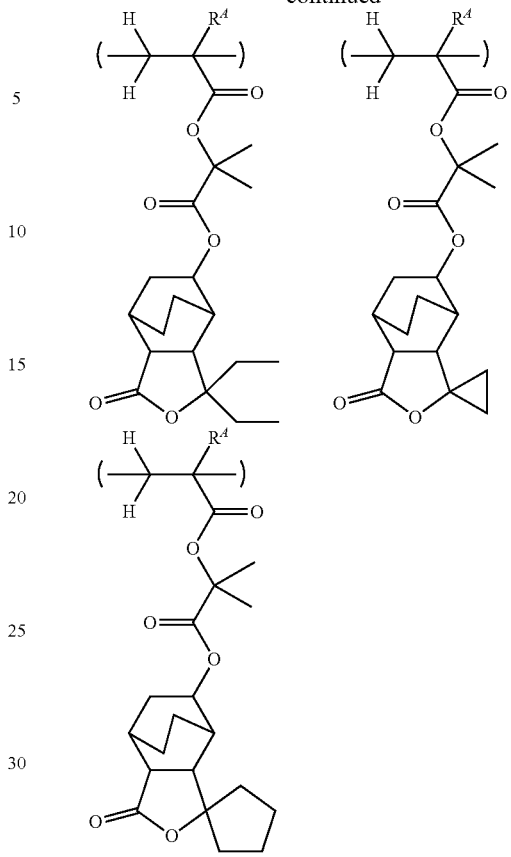

When the base polymer contains recurring units (c), the content of units (c) is preferably up to 25 mol %, more preferably up to 15 mol % of the overall recurring units. When the base polymer contains recurring units (d), the content of units (d) is preferably up to 75 mol %, more preferably up to 60 mol % of the overall recurring units. When the base polymer contains recurring units (e), the content of units (e) is preferably up to 40 mol/%, more preferably up to 25 mol % of the overall recurring units. The total content of units (c), (d) and (e) is preferably 30 to 75 mol %, more preferably 40 to 60 mol % of the overall recurring units.

Using a base polymer containing recurring units (c), a resist film having more etch resistance is formed. Using a base polymer containing recurring units (d), a resist film having better LWR is formed. Using a base polymer containing recurring units (e), a resist film pattern of profile with fully controlled footing on an underlying antireflection film is formed.

The base polymer preferably has a weight average molecular weight (Mw) of 1,000 to 50,000, more preferably 5,000 to 20,000, and even more preferably 6,000 to 12,000, as measured versus polystyrene standards by GPC using tetrahydrofuran (THF) solvent. Also the base polymer should preferably have a dispersity (Mw/Mn) of 1.0 to 3.0, more preferably 1.0 to 2.0.

The method of synthesizing the base polymer is, for example, by dissolving one or more monomers providing the desired recurring units in an organic solvent, adding a radical polymerization initiator, and heating for polymerization. The polymerization method is described in U.S. Pat. No. 9,256,127 (JP-A 2015-214634, paragraphs [0134]-[0137]).

The base polymer may be used alone or in a combination of two or more.

(D) Organic Solvent

The positive resist composition of the invention further comprises (D) an organic solvent. Any organic solvent may be used as long as the foregoing components and other additives are soluble therein. The inclusion of an organic solvent facilitates to coat the resist composition onto a substrate.

Examples of the organic solvent include ketones such as cyclohexanone and methyl-2-n-pentyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone (GBL), and mixtures thereof.

Of the above organic solvents, it is recommended to use diethylene glycol dimethyl ether, 1-ethoxy-2-propanol, PGMEA, cyclohexanone, GBL, and mixtures thereof because the PAG is most soluble therein.

An appropriate amount of the organic solvent (D) used is 200 to 5,000 parts, more preferably 400 to 4,000 parts by weight per 80 parts by weight of the base polymer (C).

(E) Third Onium Salt

The resist composition may further comprise (E) a third onium salt. The third onium salt is preferably a compound having the formula (3).

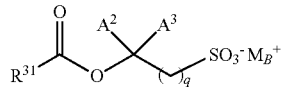
(3)

In formula (3), $A^2$ and $A^3$ are each independently hydrogen or trifluoromethyl, and q is an integer of 1 to 3. $M_B^+$ is a sulfonium, iodonium or ammonium cation. $R^{31}$ is a $C_1$-$C_{40}$ monovalent hydrocarbon group which may contain a heteroatom.

When the resist composition contains the third onium salt, its content is preferably 0.8 to 20 parts, more preferably 2 to 8 parts by weight per 80 parts by weight of the base polymer (C). The inclusion of the compound having formula (3) is effective for forming a resist film having a high sensitivity and improving DOF properties or retention performance (of isolated pattern) without sacrificing LWR. The compound having formula (3) may be used alone or in admixture.

Provided that exposure is made in an identical dose while the focus is vertically shifted, the term "DOF" refers to the range of focus that enables to form a resist pattern to a feature size, a deviation of which from the target size falls within a predetermined range, that is, the range of focus that ensures to form a resist pattern substantially faithful to the mask pattern. A larger magnitude of DOF is preferable.

(F) Epoxy Compound

In a preferred embodiment, the resist composition further comprises (F) an epoxy compound having the formula (4).

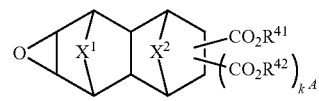
(4)

In formula (4), $X^1$ and $X^2$ are each independently —$CH_2$— or —O—, $k^A$ is 0 or 1, $R^{41}$ and $R^{42}$ are each independently a $C_4$-$C_{20}$ tertiary hydrocarbon group or a group selected from the following.

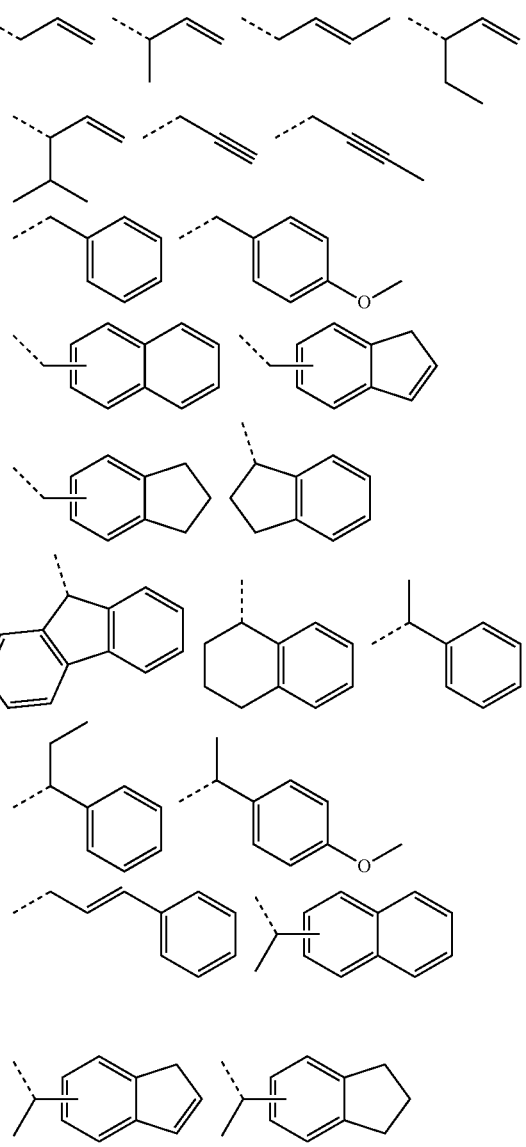

The $C_4$-$C_{20}$ tertiary hydrocarbon group is a group wherein the carbon atom attaching to the ester oxygen atom is a tertiary carbon atom. The tertiary hydrocarbon group may be a saturated or unsaturated aliphatic group. The tertiary hydrocarbon group may contain an aromatic moiety therein.

Examples of the epoxy compound having formula (4) are given below, but not limited thereto. Herein $X^1$ and $X^2$ are as defined above.

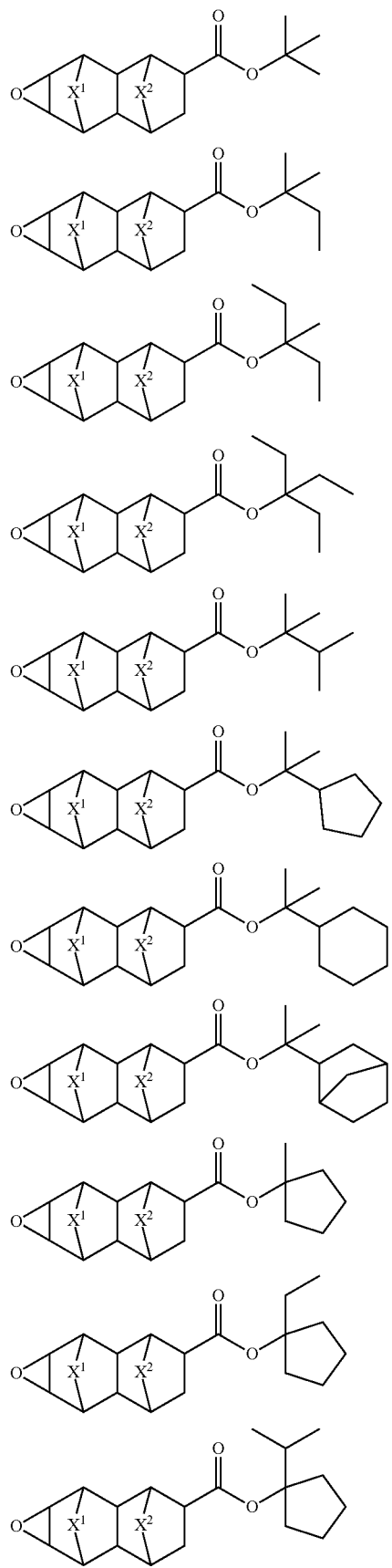
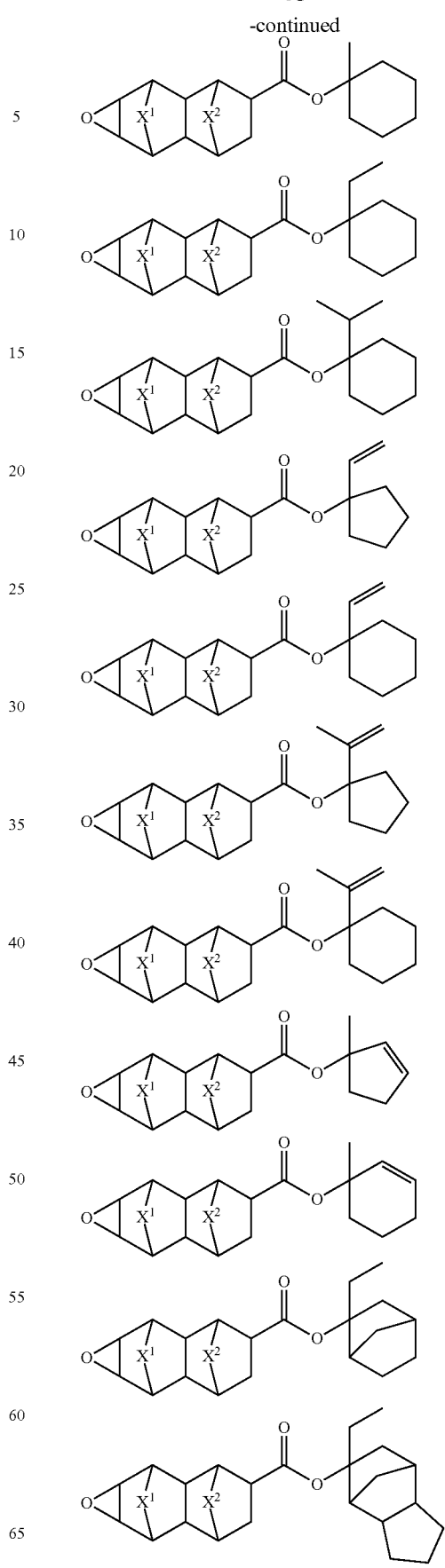

-continued

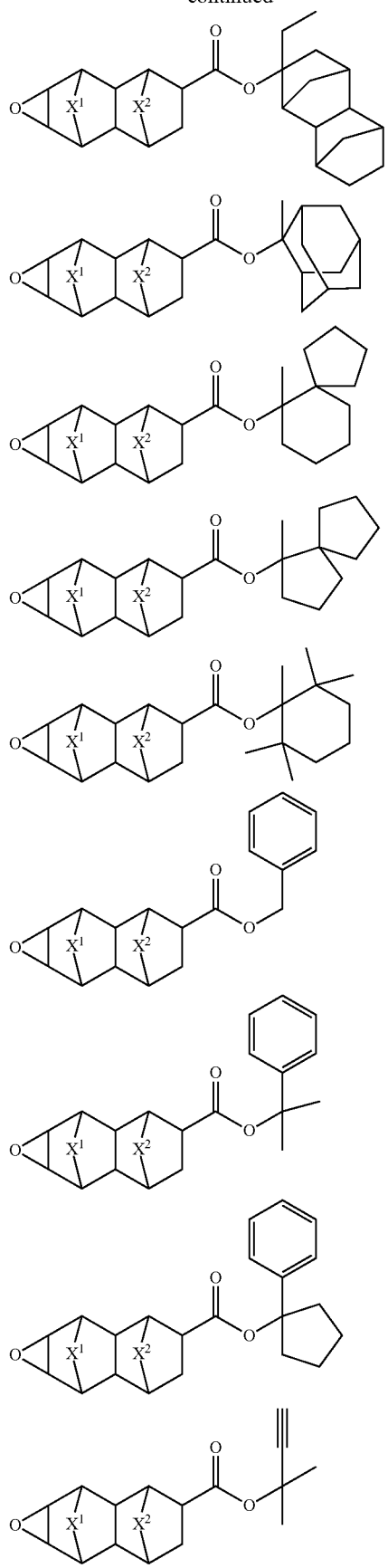

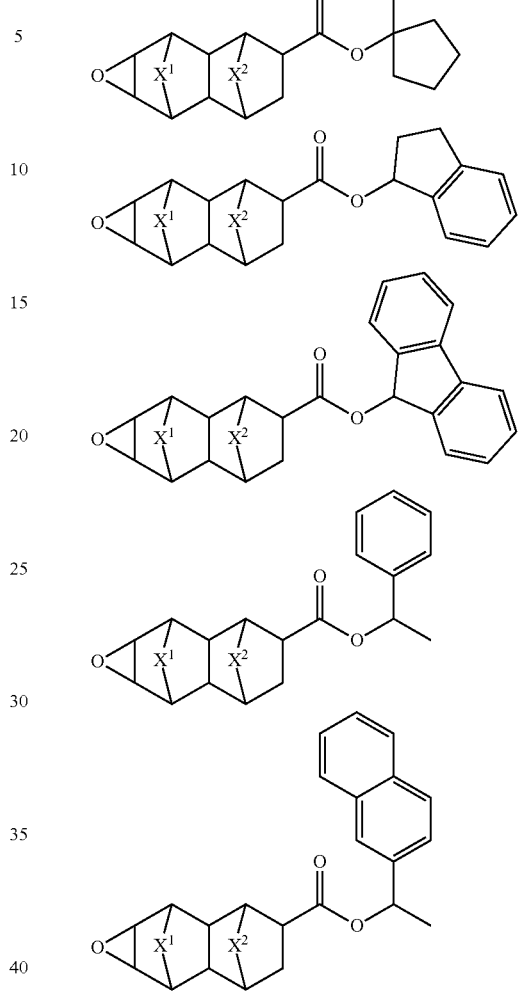

The epoxy compound may be obtained, for example, by effecting oxidation reaction on an olefin compound (pr-1) as a precursor, which can be synthesized by any well-known methods, to convert the double bond moiety to epoxide. This reaction process is shown by the following scheme, but the preparation of the epoxy compound is not limited to this route.

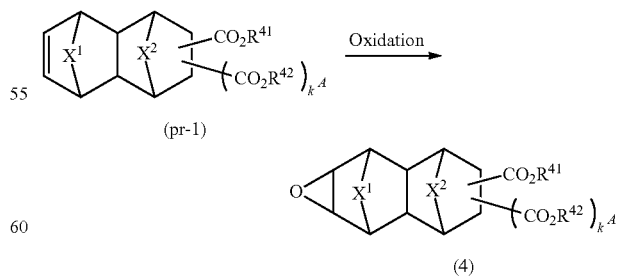

Herein $X^1$, $X^2$, $R^{41}$, $R^{42}$, and $k^A$ are as defined above.

The method for oxidizing olefin compound (pr-1) or precursor may be selected optimum from well-known oxidation methods including reactions with peroxides, for example, aqueous hydrogen peroxide, and organic carboxylic acid peroxides such as performic acid, peracetic acid, and m-chloroperbenzoic acid and catalytic reactions in the presence of transition metal oxides which are combinations of transition metal catalysts with the foregoing peroxides. Of these, aqueous hydrogen peroxide and organic carboxylic acid peroxides are preferably used because reaction runs under mild conditions at room temperature to about 40° C. without a need for complex steps.

It is desirable from the standpoint of yield that the reaction time is determined so as to drive the oxidation reaction to completion by monitoring the reaction process by gas chromatography (GC) or silica gel thin layer chromatography (TLC). Usually, the reaction time is about 1 to about 72 hours. From the reaction mixture, the epoxy compound is recovered through an ordinary aqueous workup. If necessary, it may be purified by a standard technique such as distillation, chromatography or recrystallization.

In the resist composition, the epoxy compound (F), if used, is preferably present in an amount of 0.1 to 10 parts by weight, more preferably 0.1 to 1 part by weight per 80 parts by weight of the base polymer (C). Inclusion of the epoxy compound provides the resist composition with better LWR and shelf stability. The epoxy compound may be used alone or in admixture.

(G) Fluorinated Polymer

The resist composition may further comprise (G) a fluorinated polymer comprising recurring units of at least one type selected from recurring units having the formulae (f1), (f2) and (f3).

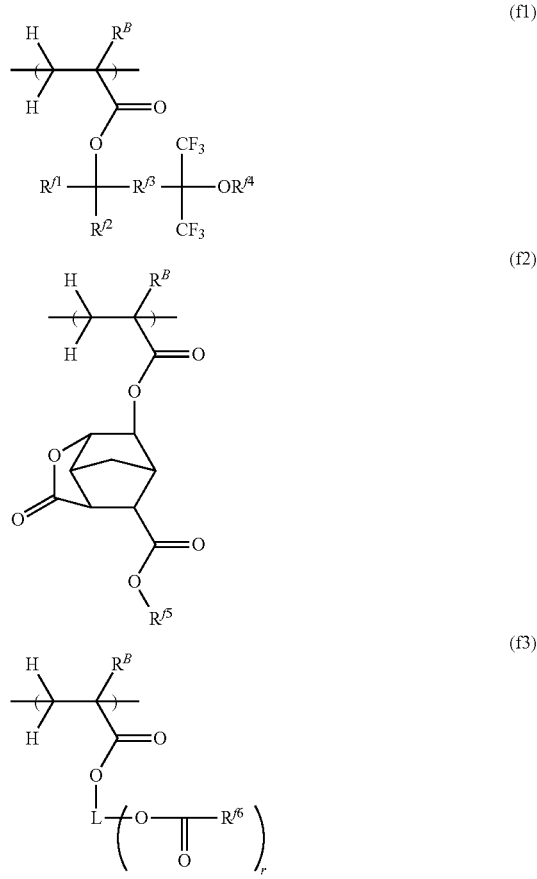

Herein $R^B$ is each independently hydrogen, fluorine, methyl or trifluoromethyl. $R^{f1}$ and $R^{f2}$ are each independently hydrogen or a $C_1$-$C_{10}$ monovalent hydrocarbon group. $R^{f3}$ is a single bond or a $C_1$-$C_5$ straight or branched divalent hydrocarbon group. $R^{f4}$ is hydrogen, a $C_1$-$C_{15}$ monovalent hydrocarbon group, $C_1$-$C_{15}$ monovalent fluorinated hydrocarbon group, or acid labile group, with the proviso that when $R^{f4}$ is a monovalent hydrocarbon group or monovalent fluorinated hydrocarbon group, an ether bond or carbonyl moiety may intervene in a carbon-carbon bond. $R^{f5}$ and $R^{f6}$ are each independently a $C_1$-$C_{10}$ monovalent fluorinated hydrocarbon group. L is a $C_1$-$C_{15}$ (r+1)-valent hydrocarbon group or $C_1$-$C_{15}$ (r+1)-valent fluorinated hydrocarbon group, wherein r is an integer of 1 to 3.

The monovalent hydrocarbon groups represented by $R^{f1}$ and $R^{f2}$ may be straight, branched or cyclic, and examples thereof include methyl, ethyl, n-propyl, isopropyl, cyclopropyl, n-butyl, isobutyl, sec-butyl, tert-butyl, cyclobutyl, n-pentyl, cyclopentyl, n-hexyl, cyclohexyl, n-heptyl, n-octyl, n-nonyl, n-decyl, adamantyl, and norbornyl. Of these, those groups of 1 to 6 carbon atoms are preferred.

The divalent hydrocarbon group represented by $R^{f3}$ may be straight, branched or cyclic, and examples thereof include methylene, ethylene, propylene, butylene, and pentylene.

The monovalent hydrocarbon group represented by $R^{f4}$ may be straight, branched or cyclic, and examples thereof include alkyl, alkenyl, and alkynyl groups, with the alkyl groups being preferred. Suitable alkyl groups include n-undecyl, n-dodecyl, tridecyl, tetradecyl and pentadecyl as well as the exemplary groups described above for the monovalent hydrocarbon groups $R^{f1}$ and $R^{f2}$. Examples of the monovalent fluorinated hydrocarbon group represented by $R^{f4}$ include the foregoing examples of the monovalent hydrocarbon group in which some or all carbon-bonded hydrogen atoms are substituted by fluorine atoms. As mentioned above, an ether bond or carbonyl moiety may intervene in a carbon-carbon bond in the foregoing groups.

Examples of the acid labile group represented by $R^{f4}$ include the exemplary groups described above for the acid labile group on the base polymer, $C_4$-$C_{20}$, preferably $C_4$-$C_{15}$ tertiary alkyl groups, trialkylsilyl groups in which each alkyl moiety has 1 to 6 carbon atoms, and $C_4$-$C_{20}$ oxoalkyl groups.

$R^{f5}$ and $R^{f6}$ represents $C_1$-$C_{10}$ monovalent fluorinated hydrocarbon groups which may be straight, branched or cyclic. Examples thereof include trifluoromethyl, 2,2,2-trifluoroethyl, 3,3,3-trifluoro-1-propyl, 3,3,3-trifluoro-2-propyl, 2,2,3,3-tetrafluoropropyl, 1,1,1,3,3,3-hexafluoroisopropyl, 2,2,3,3,4,4,4-heptafluorobutyl, 2,2,3,3,4,4,5,5-octafluoropentyl, 2,2,3,3,4,4,5,5,6,6,7,7-dodecafluoroheptyl, 2-(perfluorobutyl)ethyl, 2-(perfluorohexyl)ethyl, 2-(perfluorooctyl)ethyl, and 2-(perfluorodecyl)ethyl.

L represents a $C_1$-$C_{15}$ (r+1)-valent hydrocarbon group which may be straight, branched or cyclic. Examples thereof include methyl, ethyl, n-propyl, isopropyl, cyclopropyl, n-butyl, isobutyl, sec-butyl, tert-butyl, cyclobutyl, n-pentyl, cyclopentyl, n-hexyl, cyclohexyl, n-heptyl, n-octyl, n-nonyl, n-decyl, adamantyl and norbornyl, with a number (r) of hydrogen atoms being eliminated. L also represents a $C_1$-$C_{15}$ (r+1)-valent fluorinated hydrocarbon group which may be straight, branched or cyclic. Examples thereof include the foregoing examples of the (r+1)-valent hydrocarbon group in which some or all hydrogen atoms are substituted by fluorine atoms.

When the ArF immersion lithography is applied to the resist composition in the absence of a resist protective film, the fluorinated polymer (G) segregates on the resist film surface for achieving a function of preventing or reducing water penetration or leaching in the resist film. In the resist composition, the fluorinated polymer (G), if used, is preferably present in an amount of 1 to 12 parts by weight, more preferably 3 to 8 parts by weight per 80 parts by weight of the base polymer (C). Inclusion of the fluorinated polymer ensures that a resist pattern with further reduced defectivity is formed. The fluorinated polymer may be used alone or in admixture.

(H) Basic Compound

The resist composition may further comprise a basic compound as a quencher. Inclusion of a basic compound leads to a further improvement in resolution. Examples of the basic compound include primary, secondary, and tertiary amine compounds, specifically amine compounds having a hydroxyl group, ether bond, ester bond, lactone ring, cyano group or sulfonate bond as described in JP-A 2008-111103, paragraphs [0146]-[0164], and compounds having a carbamate group as described in JP 3790649. An appropriate amount of the basic compound, if used, is 0.1 to 4 parts by weight per 80 parts by weight of the base polymer (C). The basic compound may be used alone or in admixture.

Other Components

The resist composition may further comprise additives such as acid amplifier compounds, dissolution inhibitors and surfactants.

The acid amplifier is a compound which is decomposed with an acid to generate another acid. For example, the compounds described in JP-A 2009-269953 may be used. The amount of the acid amplifier, if used, is preferably up to 1.6 parts by weight, more preferably up to 0.8 part by weight per 80 parts by weight of the base polymer (C). An amount of the acid amplifier within the range facilitates acid diffusion control and eliminates the risk of degrading resolution and pattern profile. The acid amplifier may be used alone or in admixture.

The dissolution inhibitor is an organic acid derivative or a compound having a Mw of up to 3,000 which changes its solubility in alkaline developer under the action of an acid. For example, the compounds described in JP-A 2009-269953 may be used. The amount of the dissolution inhibitor, if used, is preferably up to 16 parts by weight, more preferably up to 12 parts by weight per 80 parts by weight of the base polymer (C). An amount of the dissolution inhibitor within the range enables to enlarge the difference in dissolution rate between exposed and unexposed regions, achieving a further improvement in resolution. The dissolution inhibitor may be used alone or in admixture.

For the surfactant, reference should be made to JP-A 2010-215608 and JP-A 2011-016746. Suitable surfactants include FC-4430 (3M), Surflon® S-381, KH-20 and KH-30 (AGC Seimi Chemical Co., Ltd.), and Olfine® E1004 (Nisshin Chemical Co., Ltd.). Partially fluorinated oxetane ring-opened polymers having the structural formula (surf-1) are also useful.

(surf-1)

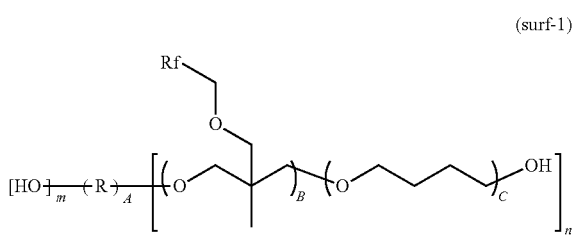

It is provided herein that R, Rf A, B, C, m, and n are applied to only formula (surf-1), independent of their descriptions other than for the surfactant. R is a di- to tetra-valent $C_2$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

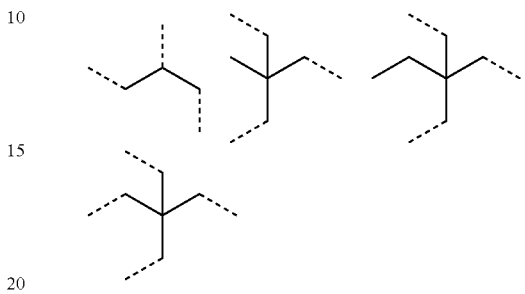

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m is an integer of 0 to 3, n is an integer of 1 to 4, and the sum of m and n, which represents the valence of R, is an integer of 2 to 4. "A" is equal to 1, B is an integer of 2 to 25, and C is an integer of 0 to 10. Preferably, B is an integer of 4 to 20, and C is 0 or 1. Note that the above structural formula does not prescribe the arrangement of respective constituent units while they may be arranged either blockwise or randomly. For the preparation of surfactants in the form of partially fluorinated oxetane ring-opened polymers, reference should be made to U.S. Pat. No. 5,650,483, for example.

If used, the surfactant is preferably formulated in an amount of 0.001 to 20 parts, and more preferably 0.01 to 10 parts by weight per 80 parts by weight of the base polymer (C). The addition of surfactant to the resist composition is effective for improving or controlling its coating. The surfactant may be used alone or in admixture.

The positive resist composition formulated as above forms a resist film which has satisfactory PED stability, is improved in DOF performance in terms of removal (or trench pattern) performance or retention (or isolated pattern) performance by virtue of moderately rounded top shape, and thus forms a pattern with reduced LWR.

While the positive resist composition is useful in the conventional lithography technology (inclusive of multilayer resist process), it is especially useful in the immersion lithography process involving the steps of forming a protective film on the resist film and exposing the resist film to radiation via water.

Further, the positive resist composition is quite useful in the LLE double patterning technology where PED stability is required. The pattern forming process using the positive resist composition is effective for suppressing any degradation of pattern profile or resolution which can otherwise occur when the immersion lithography is carried out after a conventional protective film is formed. Specifically, a pattern top shape can be moderately rounded without sacrificing the pattern height. Also the DOF performance is improved, especially the DOF performance of trench and isolated patterns is improved.

Pattern Forming Process

Another embodiment of the invention is a pattern forming process comprising the steps of applying the positive resist composition to form a resist film on a substrate, exposing the resist film to KrF excimer laser, ArF excimer laser, EB or EUV, and developing the exposed resist film in a developer to form a pattern. If necessary, any additional steps may be added.

The substrate used herein is typically a substrate for integrated circuit fabrication (e.g., Si, $SiO_2$, SiN, SiON, TiN, WSi, BPSG, SOG or organic antireflective coating) or a substrate for mask circuit fabrication (e.g., Cr, CrO, CrON, $MoSi_2$ or $SiO_2$).

The positive resist composition is applied onto a substrate by a suitable coating technique such as spin coating. The coating is prebaked on a hotplate preferably at a temperature of 60 to 150° C. for 1 to 10 minutes, more preferably at 80 to 140° C. for 1 to 5 minutes, to form a resist film of 0.05 to 2 µm thick.

The resist film is then exposed to a desired pattern of high-energy radiation such as KrF excimer laser light, ArF excimer laser light, EUV, or EB. When KrF excimer laser, ArF excimer laser or EUV is used, the resist film is exposed thereto through a mask having a desired pattern in a dose of preferably 1 to 200 $mJ/cm^2$, more preferably 10 to 100 $mJ/cm^2$. When EB is used, the resist film is exposed thereto through a mask having a desired pattern or directly in a dose of preferably 1 to 300 $µC/cm^2$, more preferably 10 to 200 $µC/cm^2$.

The exposure is generally performed by conventional lithography whereas the immersion lithography of holding a liquid having a refractive index of at least 1.0 between the resist film and a projection lens may also be employed. The liquid is typically water, and in this case, a protective film which is insoluble in water may be formed on the resist film.

While the water-insoluble protective film which is used in the immersion lithography serves to prevent any components from being leached out of the resist film and to improve water sliding on the film surface, it is generally divided into two types. The first type is an organic solvent-strippable protective film which must be stripped, prior to alkaline development, with an organic solvent in which the resist film is not dissolvable. The second type is an alkali-soluble protective film which is soluble in an alkaline developer so that it can be removed simultaneously with the removal of solubilized regions of the resist film. The protective film of the second type is preferably of a material comprising a polymer having a 1,1,1,3,3,3-hexafluoro-2-propanol residue (which is insoluble in water and soluble in an alkaline developer) as a base in an alcohol solvent of at least 4 carbon atoms, an ether solvent of 8 to 12 carbon atoms or a mixture thereof. Alternatively, a surfactant which is insoluble in water and soluble in an alkaline developer may be dissolved in an alcohol solvent of at least 4 carbon atoms, an ether solvent of 8 to 12 carbon atoms or a mixture thereof to form a material from which the protective film of the second type is formed.

After the exposure, the resist film may be baked (PEB) on a hotplate preferably at 60 to 150° C. for 1 to 5 minutes, more preferably at 80 to 140° C. for 1 to 3 minutes.

After the exposure or PEB, the resist film is developed in a developer in the form of an aqueous base solution for 0.1 to 3 minutes, preferably 0.5 to 2 minutes by conventional techniques such as dip, puddle and spray techniques. A typical developer is a 0.1 to 5 wt %, preferably 2 to 3 wt % aqueous solution of tetramethylammonium hydroxide (TMAH) or the like.

The pattern forming process may further involve the (post-soaking) step of rinsing the resist film with deionized water to extract the acid generator and other residues from the film surface or to wash away foreign particles and/or the (post-soaking) step of rinsing the resist film for removing any water remaining after the exposure step.

EXAMPLES

Synthesis Examples, Examples and Comparative Examples are given below by way of illustration and not by way of limitation. The abbreviation "pbw" is parts by weight.

[1] Synthesis of Epoxy Compound Q-1

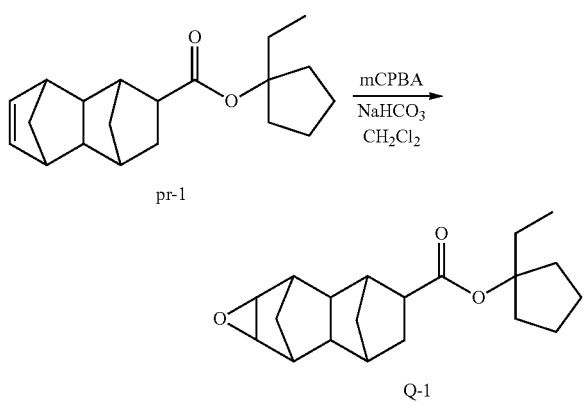

Synthesis Example 1

Under nitrogen atmosphere, 40 g of olefin compound pr-1 was mixed with 18.5 g of sodium hydrogencarbonate and 600 g of dichloromethane to form a suspension, which was ice cooled below 10° C. Below 20° C., 27 g of m-chloroperbenzoic acid was added to the suspension over 10 minutes. The solution was stirred at room temperature for 4 hours. After the complete consumption of the olefin compound was confirmed by gas chromatography, the reaction solution was ice cooled again. Below 20° C., an aqueous solution of 37 g of sodium thiosulfate pentahydrate in 500 g of water was added dropwise thereto. At the end of dropwise addition, stirring was continued at room temperature for 2 hours. The solution was combined with 1,000 g of hexane for layer separation. This was followed by consecutive washing with 200 g of water, 200 g of saturated sodium hydrogencarbonate aqueous solution, and 200 g of saturated brine. After the solvent was distilled off in vacuum, the solution was stirred at 80° C. for 2 hours, cooled at room temperature, and distilled in vacuum. There was obtained 37.9 g of Epoxy compound Q-1 (yield 90%, boiling point 150° C./10 Pa). The $^1$H-NMR spectrum of Epoxy compound Q-1 is shown in FIG. 1.

[2] Synthesis of Base Polymers

Synthesis Examples 2-1 to 2-6

Polymers P-1 to P-6 were synthesized by combining selected monomers so as to give the compositional ratio shown in Table 1, effecting copolymerization reaction in methyl ethyl ketone solvent, crystallization in methanol, repeated washing with hexane, isolation, and drying. Polymers P-1 to P-6 were determined for composition by $^1$H-NMR spectroscopy and for Mw and Mw/Mn by GPC versus polystyrene standards using THF solvent.

TABLE 1

| Polymer | Unit 1 (ratio) | Unit 2 (ratio) | Unit 3 (ratio) | Unit 4 (ratio) | Unit 5 (ratio) | Mw | Mw/Mn |
|---|---|---|---|---|---|---|---|
| Synthesis Example 2-1 | P-1 | A-2 (0.50) | B-1 (0.40) | B-2 (0.10) | — | — | 8,000 | 1.5 |
| 2-2 | P-2 | A-2 (0.45) | A-3 (0.05) | B-1 (0.35) | B-3 (0.15) | — | 10,000 | 1.6 |
| 2-3 | P-3 | A-2 (0.45) | A-4 (0.05) | B-1 (0.45) | B-2 (0.05) | — | 7,000 | 1.7 |
| 2-4 | P-4 | A-1 (0.40) | A-4 (0.10) | B-1 (0.20) | B-2 (0.10) | B-4 (0.20) | 8,000 | 1.6 |
| 2-5 | P-5 | A-1 (0.40) | A-4 (0.10) | B-2 (0.10) | B-4 (0.40) | — | 8,000 | 1.6 |
| 2-6 | P-6 | A-1 (0.40) | A-4 (0.10) | B-1 (0.35) | B-2 (0.15) | — | 8,000 | 1.6 |

Tables 2 and 3 show the structure of units in Table 1.

TABLE 2

| A-1 | A-2 | A-3 | A-4 |
|---|---|---|---|

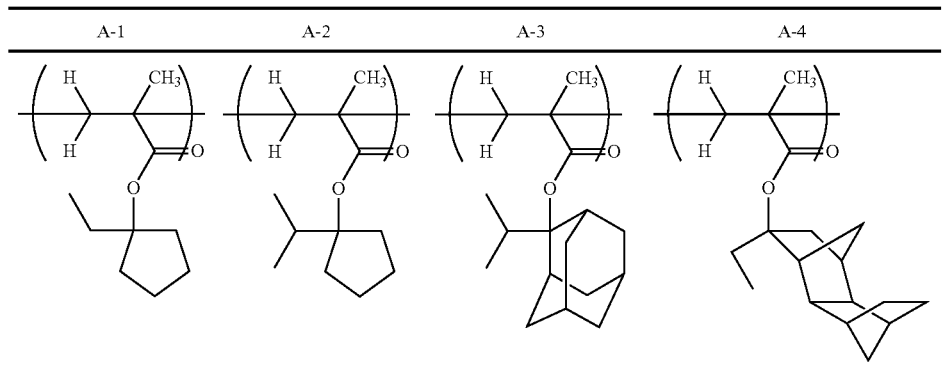

TABLE 3

| B-1 | B-2 | B-3 | B-4 |
|---|---|---|---|

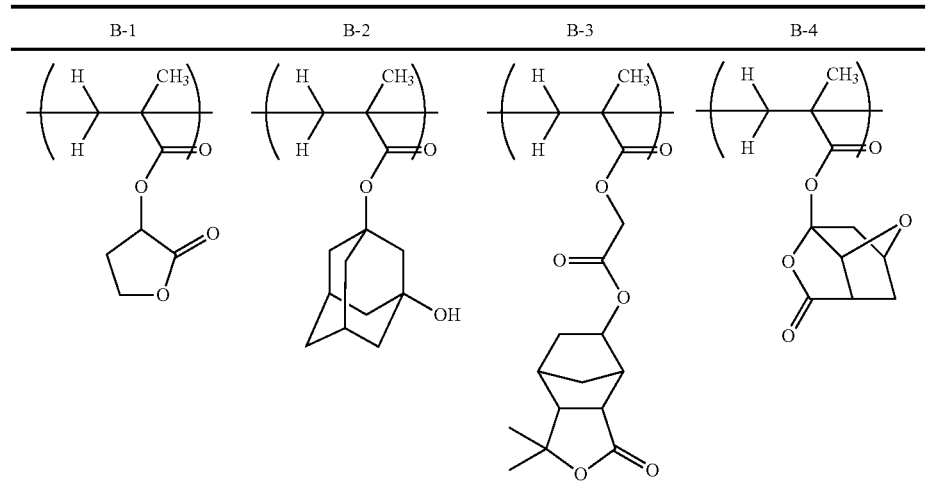

[3] Preparation of Resist Compositions

Examples 1-1 to 1-14 and Comparative Examples 1-1 to 1-23

Resist compositions in solution form were prepared by dissolving selected components in a solvent in accordance with the formulation shown in Tables 4 to 6, and filtering through a Teflon® filter with a pore size of 0.2 μm.

TABLE 4

| | Resist composition | Polymer (pbw) | Onium salt 1 (pbw) | Onium salt 2 (pbw) | Onium salt 3 (pbw) | Amine quencher (pbw) | Epoxy compound (pbw) | Fluorinated polymer (pbw) | Surfactant (pbw) | Solvent 1 (pbw) | Solvent 2 (pbw) |
|---|---|---|---|---|---|---|---|---|---|---|---|
| Example 1-1 | R-1 | P-1 (80) | A1 (5.3) | B1 (4.4) | C1 (5.3) | — | Q-1 (0-3) | I-1 (5) | F-1 (0.06) | PGMEA (2,421) | GBL (269) |

TABLE 4-continued

|  | Resist composition | Polymer (pbw) | Onium salt 1 (pbw) | Onium salt 2 (pbw) | Onium salt 3 (pbw) | Amine quencher (pbw) | Epoxy compound (pbw) | Fluorinated polymer (pbw) | Surfactant (pbw) | Solvent 1 (pbw) | Solvent 2 (pbw) |
|---|---|---|---|---|---|---|---|---|---|---|---|
| 1-2 | R-2 | P-1 (80) | A1 (7.9) | B1 (4.4) | C1 (5.3) | — | Q-1 (0-3) | I-1 (5) | F-1 (0.06) | PGMEA (2,421) | GBL (269) |
| 1-3 | R-3 | P-1 (80) | A1 (13.2) | B1 (4.4) | C1 (5.3) | — | Q-1 (0-3) | I-1 (5) | F-1 (0.06) | PGMEA (2,421) | GBL (269) |
| 1-4 | R-4 | P-1 (80) | A1 (19.8) | B1 (4.4) | C1 (5.3) | — | Q-1 (0-3) | I-1 (5) | F-1 (0.06) | PGMEA (2,421) | GBL (269) |
| 1-5 | R-5 | P-1 (80) | A1 (7.9) | B1 (3.3) | C1 (5.3) | — | Q-1 (0-3) | I-1 (5) | F-1 (0.06) | PGMEA (2,421) | GBL (269) |
| 1-6 | R-6 | P-1 (80) | A1 (7.9) | B1 (5.5) | C1 (5.3) | — | Q-1 (0-3) | I-1 (5) | F-1 (0.06) | PGMEA (2,421) | GBL (269) |
| 1-7 | R-7 | P-1 (80) | A1 (7.9) | B1 (6.7) | C1 (5.3) | — | Q-1 (0-3) | I-1 (5) | F-1 (0.06) | PGMEA (2,421) | GBL (269) |
| 1-8 | R-8 | P-1 (80) | A1 (7.9) | B1 (4.4) | C1 (2.7) | — | Q-1 (0-3) | I-1 (5) | F-1 (0.06) | PGMEA (2,421) | GBL (269) |
| 1-9 | R-9 | P-1 (80) | A1 (7.9) | B1 (4.4) | C1 (10.6) | — | Q-1 (0-3) | I-1 (5) | F-1 (0.06) | PGMEA (2,421) | GBL (269) |
| 1-10 | R-10 | P-1 (80) | A1 (7.9) | B2 (4.9) | C1 (5.3) | — | Q-1 (0-3) | I-1 (5) | F-1 (0.06) | PGMEA (2,421) | GBL (269) |
| 1-11 | R-11 | P-2 (80) | A1 (7.9) | B1 (3.9) | C1 (6.0) | — | Q-1 (0-3) | I-1 (5) | F-1 (0.06) | PGMEA (2,421) | GBL (269) |
| 1-12 | R-12 | P-1 (80) | A1 (13.2) | B1 (4.4) | C1 (5.3) | — | — | I-1 (5) | F-1 (0.06) | PGMEA (2,421) | GBL (269) |
| 1-13 | R-13 | P-2 (80) | A1 (7.9) | B1 (3.9) | C1 (6.0) | — | — | I-1 (5) | F-1 (0.06) | PGMEA (2,421) | GBL (269) |
| 1-14 | R-14 | P-3 (80) | A1 (13.2) | B1 (4.4) | C1 (5.3) | — | Q-1 (0-3) | I-1 (5) | F-1 (0.06) | PGMEA (2,421) | GBL (269) |

TABLE 5

|  |  | Resist composition | Polymer (pbw) | Onium salt 1 (pbw) | Onium salt 2 (pbw) | Onium salt 3 (pbw) | Amine quencher (pbw) | Epoxy compound (pbw) | Fluorinated polymer (pbw) | Surfactant (pbw) | Solvent 1 (pbw) | Solvent 2 (pbw) |
|---|---|---|---|---|---|---|---|---|---|---|---|---|
| Comparative Example | 1-1 | CR-1 | P-1 (80) | A1 (2.6) | B1 (4.4) | C1 (5.3) | — | Q-1 (0.3) | I-1 (5) | F-1 (0.06) | PGMEA (2,421) | GBL (269) |
|  | 1-2 | CR-2 | P-1 (80) | A1 (4.0) | B1 (4.4) | C1 (5.3) | — | Q-1 (0.3) | I-1 (5) | F-1 (0.06) | PGMEA (2,421) | GBL (269) |
|  | 1-3 | CR-3 | P-1 (80) | A1 (26.4) | B1 (4.4) | C1 (5.3) | — | Q-1 (0.3) | I-1 (3) | F-1 (0.06) | PGMEA (2,421) | GBL (269) |
|  | 1-4 | CR-4 | P-1 (80) | A1 (7.9) | — | C1 (5.3) | — | Q-1 (0.3) | I-1 (5) | F-1 (0.06) | PGMEA (2,421) | GBL (269) |
|  | 1-5 | CR-5 | P-1 (80) | A1 (7.9) | B1 (1.1) | C1 (5.3) | — | Q-1 (0.3) | I-1 (5) | F-1 (0.06) | PGMEA (2,421) | GBL (269) |
|  | 1-6 | CR-6 | P-1 (80) | A1 (7.9) | B1 (2.2) | C1 (5.3) | — | Q-1 (0.3) | I-1 (5) | F-1 (0.06) | PGMEA (2,421) | GBL (269) |
|  | 1-7 | CR-7 | P-1 (80) | A1 (7.9) | B1 (8.9) | C1 (5.3) | — | Q-1 (0.3) | I-1 (5) | F-1 (0.06) | PGMEA (2,421) | GBL (269) |
|  | 1-8 | CR-8 | P-1 (80) | A1 (7.9) | B1 (11.1) | C1 (5.3) | — | Q-1 (0.3) | I-1 (5) | F-1 (0.06) | PGMEA (2,421) | GBL (269) |
|  | 1-9 | CR-9 | P-1 (80) | A1 (7.9) | B1 (13.3) | C1 (5.3) | — | Q-1 (0.3) | I-1 (5) | F-1 (0.06) | PGMEA (2,421) | GBL (269) |
|  | 1-10 | CR-10 | P-1 (80) | A1 (7.9) | B1 (4.4) | — | — | Q-1 (0.3) | I-1 (5) | F-1 (0.06) | PGMEA (2,421) | GBL (269) |
|  | 1-11 | CR-11 | P-1 (80) | A1 (7.9) | B1 (4.4) | C1 (0.1) | — | Q-1 (0.3) | I-1 (5) | F-1 (0.06) | PGMEA (2,421) | GBL (269) |
|  | 1-12 | CR-12 | P-1 (80) | A1 (7.9) | B1 (4.4) | C1 (0.7) | — | Q-1 (0.3) | I-1 (5) | F-1 (0.06) | PGMEA (2,421) | GBL (269) |
|  | 1-13 | CR-13 | P-1 (80) | A1 (7.9) | B1 (4.4) | C1 (21.3) | — | Q-1 (0.3) | I-1 (5) | F-1 (0.06) | PGMEA (2,421) | GBL (269) |

TABLE 6

|  |  | Resist composition | Polymer (pbw) | Onium salt 1 (pbw) | Onium salt 2 (pbw) | Onium salt 3 (pbw) | Amine quencher (pbw) | Epoxy compound (pbw) | Fluorinated polymer (pbw) | Surfactant (pbw) | Solvent 1 (pbw) | Solvent 2 (pbw) |
|---|---|---|---|---|---|---|---|---|---|---|---|---|
| Comparative Example | 1-14 | CR-34 | P-1 (80) | A2 (2.2) | B3 (4.4) | C1 (5.3) | — | Q-1 (0.3) | I-1 (5) | F-1 (0.06) | PGMEA (2,421) | GBL (269) |
|  | 1-15 | CR-15 | P-1 (80) | A3 (2.5) | B1 (4.4) | C1 (5.3) | — | Q-1 (0-3) | I-1 (5) | F-1 (0.06) | PGMEA (2,421) | GBL (269) |

TABLE 6-continued

|  | Resist composition | Polymer (pbw) | Onium salt 1 (pbw) | Onium salt 2 (pbw) | Onium salt 3 (pbw) | Amine quencher (pbw) | Epoxy compound (pbw) | Fluorinated polymer (pbw) | Surfactant (pbw) | Solvent 1 (pbw) | Solvent 2 (pbw) |
|---|---|---|---|---|---|---|---|---|---|---|---|
| 1-16 | CR-16 | P-1 (80) | A4 (3.4) | B3 (4.4) | C1 (5.3) | — | Q-1 (0-3) | I-1 (5) | F-1 (0.06) | PGMEA (2,421) | GBL (269) |
| 1-17 | CR-17 | P-1 (80) | A1 (7.9) | — | C1 (5.3) | AQ-1 (0.743) | Q-1 (0-3) | I-1 (5) | F-1 (0.06) | PGMEA (2,421) | GBL (269) |
| 1-18 | CR-18 | P-1 (80) | A1 (7.9) | — | C1 (5.3) | AQ-2 (1.078) | Q-1 (0-3) | I-1 (5) | F-1 (0.06) | PGMEA (2,421) | GBL (269) |
| 1-19 | CR-19 | P-3 (80) | A1 (7.9) | — | C1 (5.3) | AQ-3 (1.313) | Q-1 (0-3) | I-1 (5) | F-1 (0.06) | PGMEA (2,421) | GBL (269) |
| 1-20 | CR-20 | P-1 (80) | A1 (7.9) | B3 (4.3) | C1 (5.3) | — | Q-1 (0-3) | I-1 (5) | F-1 (0.06) | PGMEA (2,421) | GBL (269) |
| 1-21 | CR-21 | P-4 (80) | A1 (7.9) | B1 (4.4) | C1 (5.3) | — | Q-1 (0-3) | I-1 (5) | F-1 (0.06) | PGMEA (2,421) | GBL (269) |
| 1-22 | CR-22 | P-5 (80) | A1 (7.9) | B1 (4.4) | C1 (5.3) | — | Q-1 (0-3) | I-1 (5) | F-3 (0.06) | PGMEA (2,421) | GBL (269) |
| 1-23 | CR-23 | P-6 (80) | A1 (7.9) | B1 (4.4) | C1 (5.3) | — | Q-1 (0-3) | I-1 (5) | F-1 (0.06) | PGMEA (2,421) | GBL (269) |

In Tables 4 to 6, the solvent, onium salt 1 (A1 to A4), onium salt 2 (B1 to B3), onium salt 3 (C1), amine quencher (AQ-1 to AQ-3), epoxy compound (Q-1), fluorinated polymer (I-1), and surfactant (F-1) are identified below.

Solvent:
 PGMEA=propylene glycol monomethyl ether acetate
 GBL=γ-butyrolactone

Onium Salt 1: A1 to A4

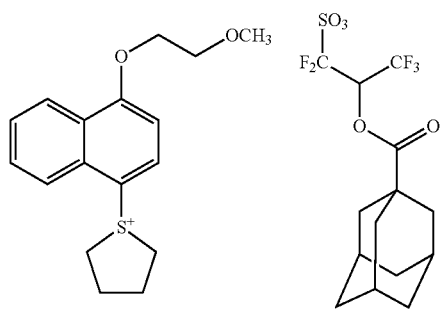

A1

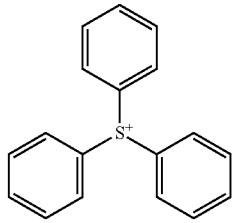

A2

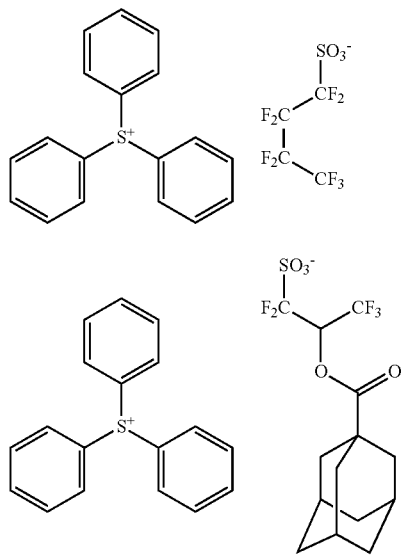

A3

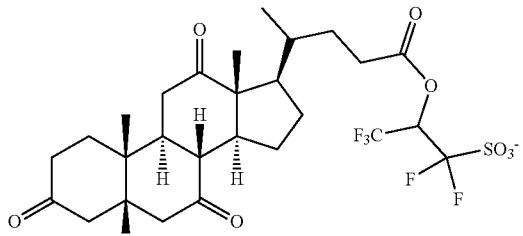

A4

Onium Salt 2: B1 to B3

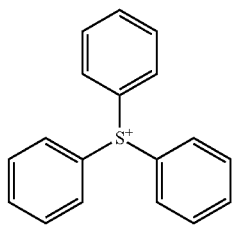

B1

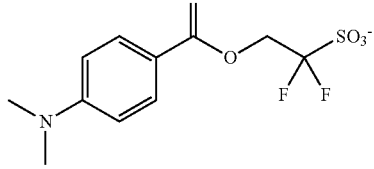

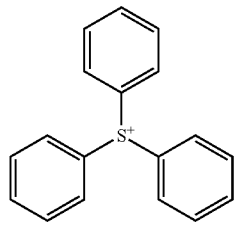
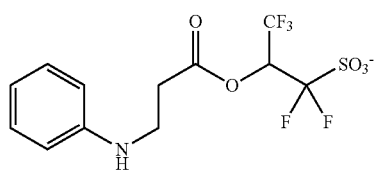
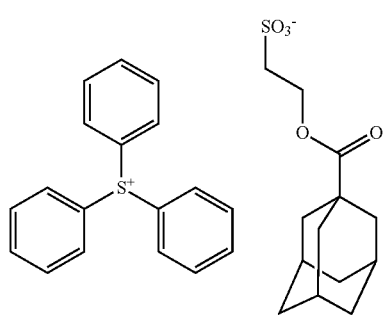
Onium Salt 3: C1
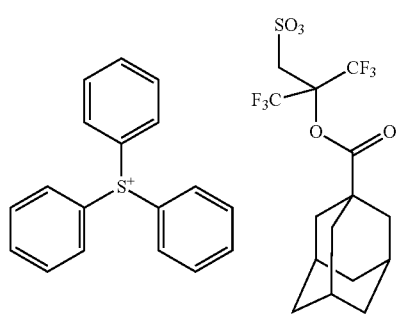
Amine Quencher: AQ-1 to AQ-3
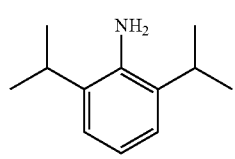
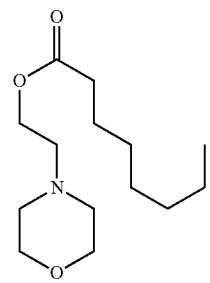
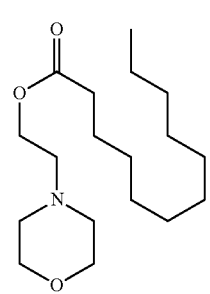
Epoxy Compound: Q-1
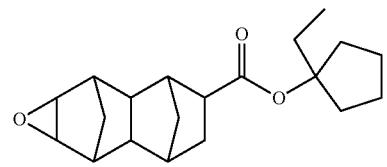
Fluorinated Polymer: I-1
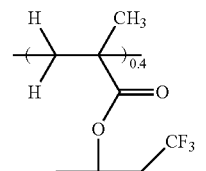
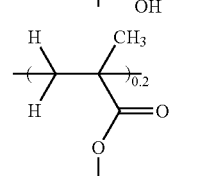
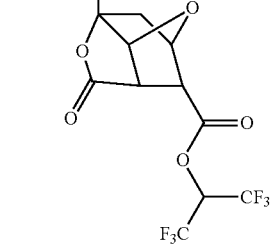

-continued

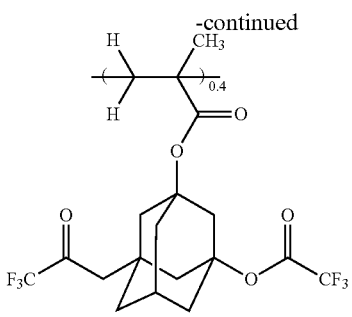

Surfactant F-1: 3-methyl-3-(2,2,2-trifluoroethoxymethyl) oxetane/tetrahydrofuran/2,2-dimethyl-1,3-propanediol copolymer (Omnova Solutions, Inc.)

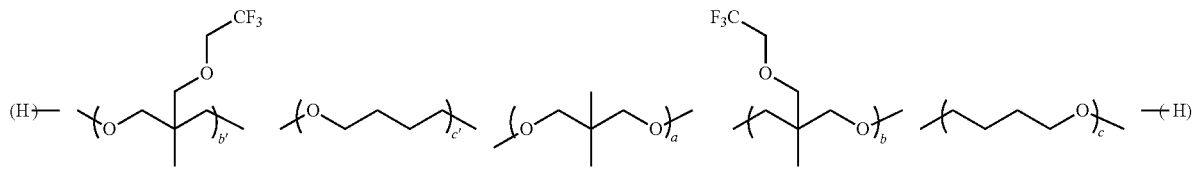

a:(b+b'):(c+c')=1:4-7:0.01-1 (molar ratio)
Mw=1.500

[4] Evaluation of Resist Compositions

Examples 2-1 to 2-14 and Comparative Examples 2-1 to 2-23

On a silicon substrate, an antireflective coating solution (ARC29A, Nissan Chemical Corp.) was coated and baked at 180° C. for 60 seconds to form an ARC of 100 nm thick Each of the resist compositions (R-1 to R-14, CR-1 to CR-23) was spin coated onto the ARC and prebaked on a hotplate at 100° C. for 60 seconds to form a resist film of 90 nm thick on the ARC. Using an ArF excimer laser scanner (NSR—S610C by Nikon Corp., NA 1.30, σ 0.94/0.74, dipole 35 deg, illumination, binary mask), the resist film was exposed according to the immersion lithography. The immersion liquid used herein was water. Thereafter, the resist film was baked (PEB) at 85° C. for 60 seconds and developed in a 2.38 wt % TMAH aqueous solution for 60 seconds, forming a line-and-space (L/S) pattern.

Example 2-15

A L/S pattern was formed as in Example 2-11 except that a water-repellent protective film solution (IOC-301 by Shin-Etsu Chemical Co., Ltd.) was spin coated onto the resist film and baked on a hotplate at 90° C. for 60 seconds to form a water-repellent protective film of 50 nm thick on the resist film.

The resist composition was evaluated for LWR, DOF and PED stability by the following methods.

A chromium pattern of 82 nm pitch and 37 nm size was observed under an electron microscope. The optimum dose Eop is the dose (mJ/cm$^2$) at which a space width of 45 nm is finished. A smaller value of Eop indicates a higher sensitivity.

Exposure was performed at Eop while shifting the focus up and down. A range (nm) of focus within which a US pattern was resolved to a target size of 45 nm±10% (i.e., 40.5 to 49.5 nm) was determined and reported as DOF. A greater value indicates a wider margin relative to focus shifts, i.e., better performance.

On a L/S pattern printed at the optimum dose Eop, the space width is measured at longitudinally spaced apart 60 points, from which a 3-fold value (3σ) of standard deviation (σ) is determined and reported as LWR. A smaller value of 3σ indicates a pattern having a lower roughness and more uniform space width.

A pattern was formed at the dose at which a pattern of 52 nm line width and 104 nm pitch is printed to a line width 52 nm. A line width (CD0) obtained from PEB immediately after exposure, and a line width (CD$_{90}$) obtained from PEB after 90 minutes from exposure were measured. A change of line width was computed according to the following formula:

change of line width (%)=100×|CD$_{90}$−CD$_0$|/52 and reported as PED stability. A smaller change of line width indicates better stability.

The results are shown in Tables 7 to 9.

TABLE 7

| | | Resist composition | Eop (mJ/cm$^2$) | DOF (nm) | LWR (nm) | PED stability (%) |
|---|---|---|---|---|---|---|
| Example | 2-1 | R-1 | 38.7 | 180 | 2.9 | 2.4 |
| | 2-2 | R-2 | 33.2 | 210 | 2.8 | 2.5 |
| | 2-3 | R-3 | 27.0 | 210 | 2.9 | 2.6 |
| | 2-4 | R-4 | 23.5 | 150 | 3.0 | 2.6 |
| | 2-5 | R-5 | 30.4 | 150 | 3.0 | 2.6 |
| | 2-6 | R-6 | 38.0 | 180 | 2.9 | 2.4 |
| | 2-7 | R-7 | 41.6 | 150 | 2.8 | 2.2 |
| | 2-8 | R-8 | 39.0 | 150 | 3.0 | 2.5 |
| | 2-9 | R-9 | 28.9 | 150 | 3.0 | 2.5 |
| | 2-10 | R-10 | 28.4 | 210 | 2.8 | 2.5 |
| | 2-11 | R-11 | 30.8 | 270 | 2.6 | 2.5 |
| | 2-12 | R-12 | 26.2 | 210 | 3.1 | 2.6 |
| | 2-13 | R-13 | 29.2 | 270 | 2.8 | 2.5 |
| | 2-14 | R-14 | 27.1 | 180 | 3.0 | 2.7 |
| | 2-15 | R-11 | 27.7 | 210 | 2.8 | 2.6 |

TABLE 8

| | | Resist composition | Eop (mJ/cm$^2$) | DOF (nm) | LWR (nm) | PED stability (%) |
|---|---|---|---|---|---|---|
| Comparative Example | 2-1 | CR-1 | 50.0 | 120 | 3.0 | 2.2 |
| | 2-2 | CR-2 | 43.4 | 120 | 3.0 | 2.3 |
| | 2-3 | CR-3 | — | 0 | — | — |
| | 2-4 | CR-4 | — | 0 | — | — |
| | 2-5 | CR-5 | — | 0 | — | — |
| | 2-6 | CR-6 | 25.9 | 90 | 3.1 | 3.1 |
| | 2-7 | CR-7 | 48.4 | 120 | 2.8 | 2.2 |
| | 2-8 | CR-8 | 54.7 | 90 | 2.9 | 2.1 |
| | 2-9 | CR-9 | — | 0 | — | — |
| | 2-10 | CR-10 | 47 | 120 | 3.6 | 2.4 |
| | 2-11 | CR-11 | 46.8 | 120 | 3.7 | 2.4 |

TABLE 8-continued

| Resist composition | Eop (mJ/cm²) | DOF (nm) | LWR (nm) | PED stability (%) |
|---|---|---|---|---|
| 2-12 CR-12 | 45.4 | 120 | 3.3 | 2.5 |
| 2-13 CR-13 | — | 0 | — | — |

TABLE 9

| | Resist composition | Eop (mJ/cm²) | DOF (nm) | LWR (nm) | PED stability (%) |
|---|---|---|---|---|---|
| Comparative Example | 2-14 CR-14 | 43.2 | 90 | 3.1 | 2.7 |
| | 2-15 CR-15 | 45.0 | 120 | 3.1 | 2.7 |
| | 2-16 CR-16 | 49.2 | 60 | 3.2 | 2.6 |
| | 2-17 CR-17 | 31.4 | 120 | 3.0 | 6.0 |
| | 2-18 CR-18 | 31.8 | 120 | 3.6 | 2.6 |
| | 2-19 CR-19 | — | 0 | — | — |
| | 2-20 CR-20 | 22.5 | 210 | 2.8 | 4.0 |
| | 2-21 CR-21 | 45.6 | 90 | 3.4 | 2.6 |
| | 2-22 CR-22 | — | 0 | — | — |
| | 2-23 CR-23 | — | 0 | — | — |

As is evident from Tables 7 to 9, the positive resist compositions within the scope of the invention show satisfactory results including a DOF value of 150 or higher, a LWR value of 2.6 to 3.1, and a size change by PED of up to 2.7%. By contrast, the comparative positive resist compositions are inferior in all of DOF, LWR and PED stability.

Japanese Patent Application No. 2019-040330 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A positive resist composition comprising:
   (A) 4.1 to 20 parts by weight of a first onium salt having the formula (1),
   (B) 2.3 to 8.8 parts by weight of a second onium salt having the formula (2),
   (C) 80 parts by weight of a base polymer adapted to increase alkaline solubility under the action of acid, the base polymer comprising acid labile group-containing recurring units having the formula (a) and optionally acid labile group-containing recurring units having the formula (b), with the proviso that when the acid labile group-containing recurring units having formula (b) are included, those recurring units containing an acid labile group of at least 14 carbon atoms may be included in an amount of up to 5 mol % of the overall recurring units, and
   (D) 200 to 5,000 parts by weight of an organic solvent,

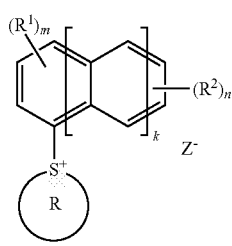
(1)

wherein $R^1$ and $R^2$ each are a hydroxyl group or a $C_1$-$C_{30}$ monovalent hydrocarbon group which may contain a heteroatom, R forms an aliphatic ring of 4 or 5 carbon atoms with $S^+$, m and n each are 0 or 1, k is 0 or 1, and $Z^-$ is an organic anion,

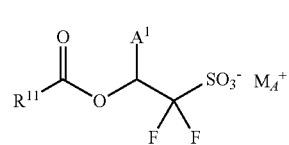
(2)

wherein $A^1$ is hydrogen or trifluoromethyl, $R^{11}$ is a group having the formula (2-1):

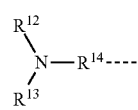
(2-1)

wherein $R^{12}$ and $R^{13}$ are each independently hydrogen or a $C_1$-$C_{20}$ monovalent hydrocarbon group which may contain a heteroatom, $R^{101}$ and $R^{102}$ may bond together to form a ring with the nitrogen atom to which they are attached, $R^{14}$ is a $C_1$-$C_{20}$ divalent hydrocarbon group which may contain a heteroatom, the broken line designates a valence bond, and $M_A^+$ is a sulfonium cation having the formula (2A) or iodonium cation having the formula (2B):

wherein $R^{101}$, $R^{102}$, $R^{103}$, $R^{104}$ and $R^{105}$ are each independently a $C_1$-$C_{20}$ monovalent hydrocarbon group which may contain a heteroatom, any two or more of $R^{101}$, $R^{102}$ and $R^{103}$ may bond together to form a ring with the sulfur atom to which they are attached,

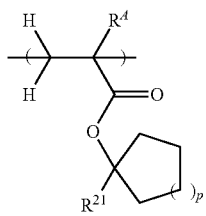
(a)

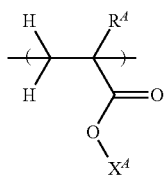
(b)

wherein $R^A$ is hydrogen or methyl, $R^{21}$ is a $C_1$-$C_8$ straight or branched alkyl group, p is an integer of 1 to 3, and $X^A$ is an acid labile group other than the group having the formula (b1):

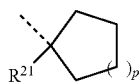
(b1)

wherein $R^{21}$ and p are as defined above, and the broken line designates a valence bond.

2. The resist composition of claim 1 wherein $X^A$ is an acid labile group having the formula (L1), (L2) or (L3):

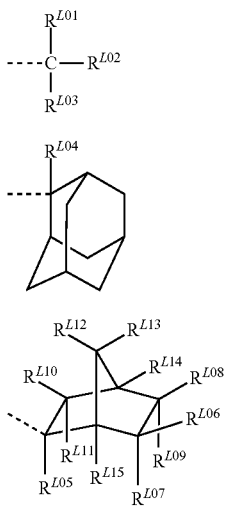
(L1)

(L2)

(L3)

wherein the broken line designates a valence bond, $R^{L01}$ to $R^{L03}$ are each independently hydrogen or a $C_1$-$C_{12}$ alkyl group, $R^{L04}$ is hydrogen or a $C_1$-$C_3$ straight or branched alkyl group, $R^{L05}$ to $R^{L15}$ are each independently hydrogen or a $C_1$-$C_6$ monovalent hydrocarbon group.

3. The resist composition of claim 1 wherein the base polymer further comprises recurring units of at least one type selected from recurring units having the formulae (c) to (e):

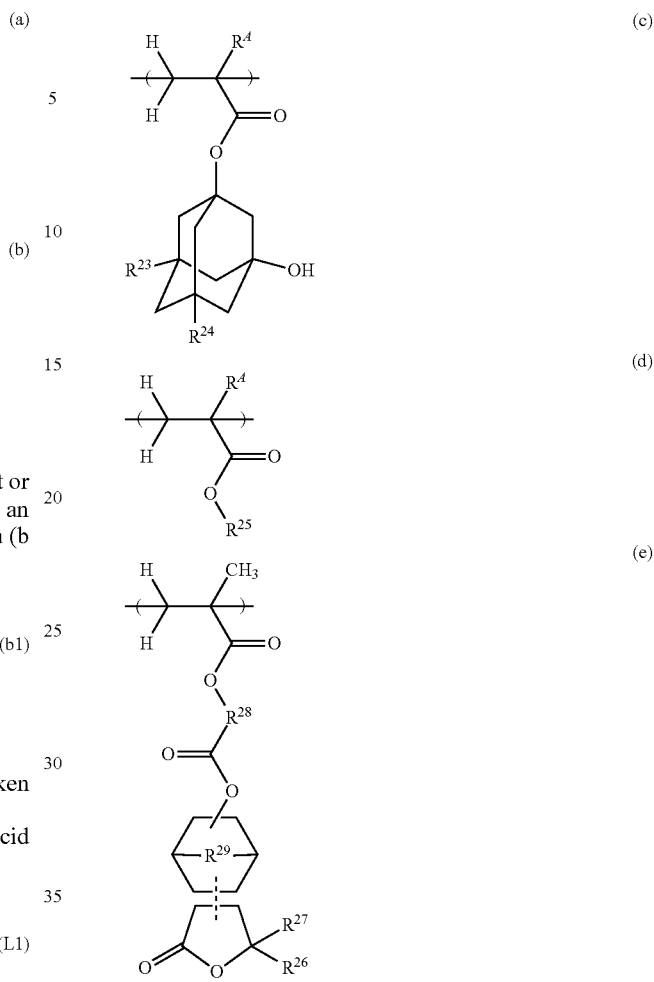
(c)

(d)

(e)

wherein $R^A$ is each independently hydrogen or methyl, $R^{23}$ and $R^{24}$ are each independently hydrogen or hydroxyl, $R^{25}$ is a substituent group containing a lactone structure, $R^{26}$ and $R^{27}$ are each independently hydrogen or $C_1$-$C_{15}$ alkyl, at least one of $R^{26}$ and $R^{27}$ being $C_1$-$C_{15}$ alkyl, $R^{26}$ and $R^{27}$ may bond together to form a ring with the carbon atom to which they are attached, a combination of $R^{26}$ and $R^{27}$ being a $C_2$-$C_{15}$ alkanediyl group, $R^{28}$ is a $C_1$-$C_{20}$ divalent hydrocarbon group in which any constituent —$CH_2$— may be replaced by —O— or —C(=O)—, $R^{29}$ is —$CH_2$—, —$CH_2CH_2$— or —O—, or two separate —H, and the dotted line designates a single bond or divalent organic group between the norbornane ring, bicyclo[2.2.2]octane ring, 7-oxanorbornane ring or cyclohexane ring structure and the γ-butyrolactone ring structure, or a structure sharing one or two constituent carbon atoms between these ring structures.

4. A positive resist composition comprising:
(A) 4.1 to 20 parts by weight of a first onium salt having the formula (1),
(B) 2.3 to 8.8 parts by weight of a second onium salt having the formula (2),
(C) 80 parts by weight of a base polymer adapted to increase alkaline solubility under the action of acid, the base polymer comprising acid labile group-containing recurring units having the formula (a) and optionally acid labile group-containing recurring units having the formula (b), with the proviso that when the acid labile group-containing recurring units having formula (b) are included, those recurring units containing an acid labile group of at least 14 carbon atoms may be included in an amount of up to 5 mol % of the overall recurring units, and (D) 200 to 5,000 parts by weight of an organic solvent,

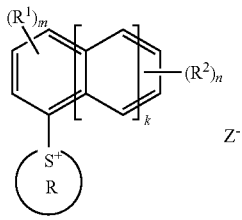
(1)

wherein $R^1$ and $R^2$ each are a hydroxyl group or a $C_1$-$C_{30}$ monovalent hydrocarbon group which may contain a heteroatom, R forms an aliphatic ring of 4 or 5 carbon atoms with $S^+$, m and n each are 0 or 1, k is 0 or 1, and $Z^-$ is an organic anion,

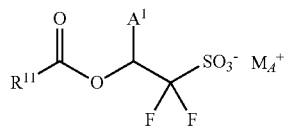
(2)

wherein $A^1$ is hydrogen or trifluoromethyl, $R^{11}$ is a nitrogen-containing heterocyclic group or a group having the formula (2-1):

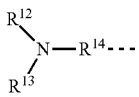
(2-1)

wherein $R^{12}$ and $R^{13}$ are each independently hydrogen or a $C_1$-$C_{20}$ monovalent hydrocarbon group which may contain a heteroatom, $R^{12}$ and $R^{13}$ may bond together to form a ring with the nitrogen atom to which they are attached, $R^{14}$ is a $C_1$-$C_{20}$ divalent hydrocarbon group which may contain a heteroatom, the broken line designates a valence bond, and $M_A^+$ is a sulfonium cation having the formula (2A) or iodonium cation having the formula (2B):

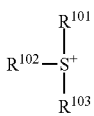
(2A)

(2B)

wherein $R^{101}$, $R^{102}$, $R^{103}$, $R^{104}$ and $R^{105}$ a R are each independently a $C_1$-$C_{20}$ monovalent hydrocarbon group which may contain a heteroatom, any two or more of $R^{101}$, $R^{102}$ and $R^{103}$ may bond together to form a ring with the sulfur atom to which they are attached,

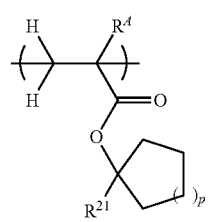
(a)

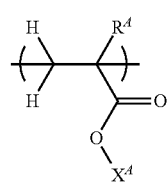
(b)

wherein $R^A$ is hydrogen or methyl, $R^{21}$ is a $C_1$-$C_8$ straight or branched alkyl group, p is an integer of 1 to 3, and $X^A$ is an acid labile group other than the group having the formula (b 1):

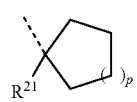
(b1)

wherein $R^{21}$ and p are as defined above, and the broken line designates a valence bond, and further comprising 0.8 to 20.0 parts by weight of a third onium salt having the formula (3):

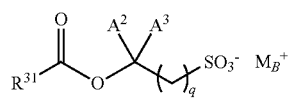
(3)

wherein $A^2$ and $A^3$ are each independently hydrogen or trifluoromethyl, q is an integer of 1 to 3, $M_B^+$ is a sulfonium, iodonium or ammonium cation, and $R^{31}$ is a $C_1$-$C_{40}$ monovalent hydrocarbon group which may contain a heteroatom.

5. A positive resist composition comprising:
(A) 4.1 to 20 parts by weight of a first onium salt having the formula (1),
(B) 2.3 to 8.8 parts by weight of a second onium salt having the formula (2),
(C) 80 parts by weight of a base polymer adapted to increase alkaline solubility under the action of acid, the base polymer comprising acid labile group-containing recurring units having the formula (a) and optionally acid labile group-containing recurring units having the formula (b), with the proviso that when the acid labile group-containing recurring units having formula (b) are included, those recurring units containing an acid labile group of at least 14 carbon atoms may be included in an amount of up to 5 mol % of the overall recurring units, and (D) 200 to 5,000 parts by weight of an organic solvent,

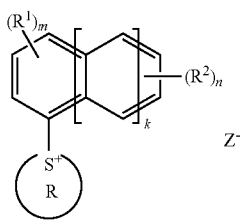

(1)

wherein $R^1$ and $R^2$ each are a hydroxyl group or a $C_1$-$C_{30}$ monovalent hydrocarbon group which may contain a heteroatom, R forms an aliphatic ring of 4 or 5 carbon atoms with $S^+$, m and n each are 0 or 1, k is 0 or 1, and $Z^-$ is an organic anion,

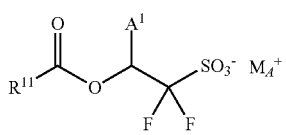

(2)

wherein $A^1$ is hydrogen or trifluoromethyl, $R^{11}$ is a nitrogen-containing heterocyclic group or a group having the formula (2-1):

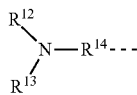

(2-1)

wherein $R^{12}$ and $R^{13}$ are each independently hydrogen or a $C_1$-$C_{20}$ monovalent hydrocarbon group which may contain a heteroatom, $R^{12}$ and $R^{13}$ may bond together to form a ring with the nitrogen atom to which they are attached, $R^{14}$ is a $C_1$-$C_{20}$ divalent hydrocarbon group which may contain a heteroatom, the broken line designates a valence bond, and $M_A^+$ is a sulfonium cation having the formula (2A) or iodonium cation having the formula (2B):

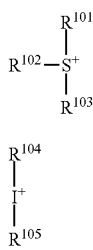

(2A)

(2B)

wherein $R^{101}$, $R^{102}$, $R^{103}$, $R^{104}$ and $R^{105}$ are each independently a $C_1$-$C_{20}$ monovalent hydrocarbon group which may contain a heteroatom, any two or more of $R^{101}$, $R^{102}$ and $R^{103}$ may bond together to form a ring with the sulfur atom to which they are attached,

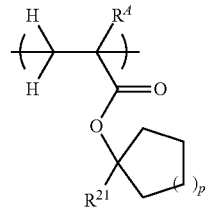

(a)

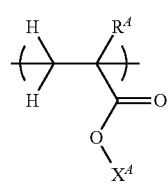

(b)

wherein $R^A$ is hydrogen or methyl, $R^{21}$ is a $C_1$-$C_8$ straight or branched alkyl group, p is an integer of 1 to 3, and $X^A$ is an acid labile group other than the group having the formula (b 1):

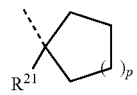

(b1)

wherein $R^{21}$ and p are as defined above, and the broken line designates a valence bond, and further comprising a compound having the formula (4):

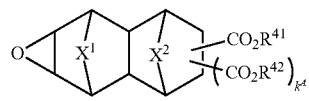

(4)

wherein $X^1$ and $X^2$ are each independently —$CH_2$— or —O—, $k^A$ is 0 or 1, $R^{41}$ and $R^{42}$ are each independently a $C_4$-$C_{20}$ tertiary hydrocarbon group or a group selected from the following:

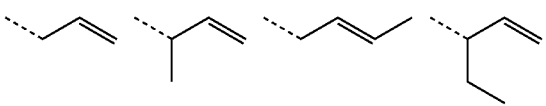

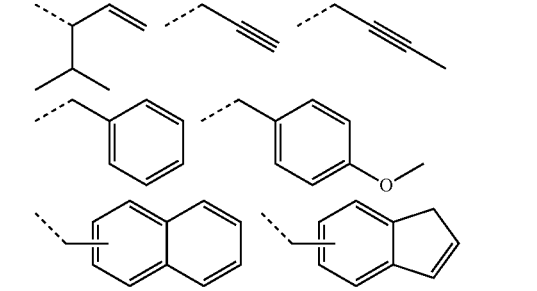

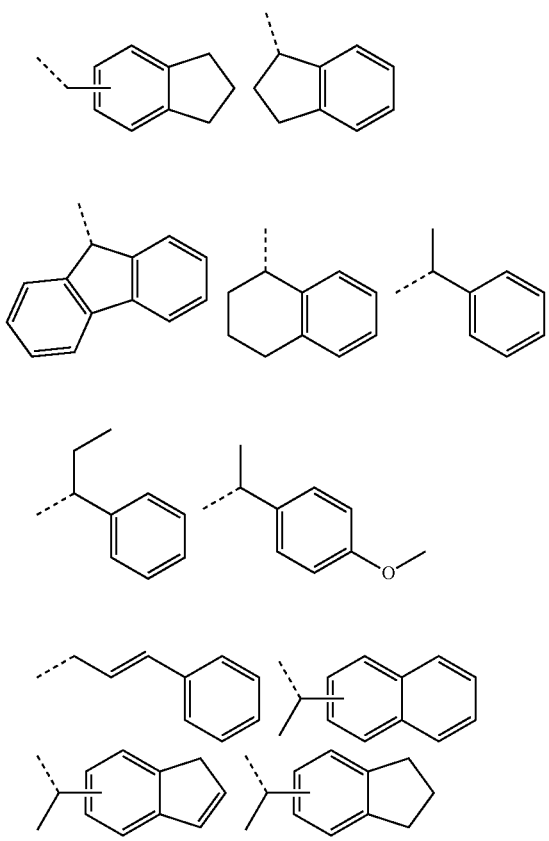

wherein the broken line designates a valence bond.

6. The resist composition of claim 1, further comprising a fluorinated polymer comprising recurring units of at least one type selected from recurring units having the formulae (f1), (f2) and (f3):

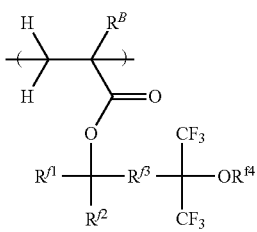

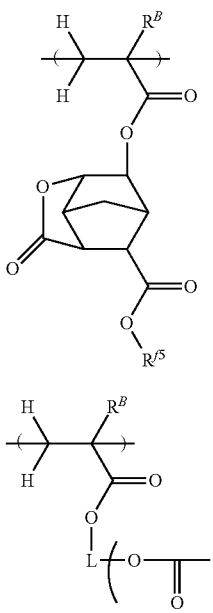

wherein $R^B$ is each independently hydrogen, fluorine, methyl or trifluoromethyl, $R^{f1}$ and $R^{f2}$ are each independently hydrogen or a $C_1$-$C_{10}$ monovalent hydrocarbon group, $R^{f3}$ is a single bond or a $C_1$-$C_5$ straight or branched divalent hydrocarbon group, $R^{f4}$ is hydrogen, a $C_1$-$C_{15}$ monovalent hydrocarbon group, $C_1$-$C_{15}$ monovalent fluorinated hydrocarbon group, or acid labile group, with the proviso that when $R^{f4}$ is a monovalent hydrocarbon group or monovalent fluorinated hydrocarbon group, an ether bond or carbonyl moiety may intervene in a carbon-carbon bond, $R^{f5}$ and $R^{f6}$ are each independently a $C_1$-$C_{10}$ monovalent fluorinated hydrocarbon group, L is a $C_1$-$C_{15}$ (r+1)-valent hydrocarbon group or $C_1$-$C_{15}$ (r+1)-valent fluorinated hydrocarbon group, and r is an integer of 1 to 3.

7. A pattern forming process comprising the steps of applying the positive resist composition of claim 1 to form a resist film on a substrate, exposing the resist film to KrF excimer laser, ArF excimer laser, EB or EUV, and developing the exposed resist film in a developer.

8. The pattern forming process of claim 7 wherein the exposing step is carried out by immersion lithography while a liquid having a refractive index of at least 1.0 is held between the resist film and a projection lens.

9. The pattern forming process of claim 8, further comprising the step of forming a protective film on the resist film, wherein immersion lithography is carried out while the liquid is held between the protective film and the projection lens.

* * * * *